US008465697B2

(12) United States Patent
Erickson et al.

(10) Patent No.: US 8,465,697 B2
(45) Date of Patent: Jun. 18, 2013

(54) SYSTEM AND METHOD FOR REGULATING FLOW IN FLUIDIC DEVICES

(75) Inventors: Gary L. Erickson, College Station, TX (US); Craig Ranger, Glendale, WI (US)

(73) Assignee: O.I. Corporation, College State, TX (US)

( * ) Notice: Subject to any disclaimer, the term of this patent is extended or adjusted under 35 U.S.C. 154(b) by 0 days.

(21) Appl. No.: 12/811,359

(22) PCT Filed: Dec. 31, 2008

(86) PCT No.: PCT/US2008/088665

§ 371 (c)(1), (2), (4) Date: Nov. 12, 2010

(87) PCT Pub. No.: WO2009/086556

PCT Pub. Date: Jul. 9, 2009

(65) Prior Publication Data

US 2011/0045599 A1 Feb. 24, 2011

Related U.S. Application Data

(60) Provisional application No. 61/017,867, filed on Dec. 31, 2007, provisional application No. 61/137,027, filed on Jul. 25, 2008.

(51) Int. Cl.

*G01N 15/06* (2006.01)
*G01N 33/00* (2006.01)
*G01N 33/48* (2006.01)

(52) U.S. Cl.

USPC ................ 422/81; 422/68.1; 422/82; 436/43; 436/52; 436/53; 436/174; 436/180

(58) Field of Classification Search

USPC .................. 422/68.1, 81, 82; 436/43, 52, 53, 436/174, 180

See application file for complete search history.

(56) References Cited

U.S. PATENT DOCUMENTS

| | | | | |
|---|---|---|---|---|
| 3,398,689 | A | 8/1968 | Allington | |
| 4,347,131 | A * | 8/1982 | Brownlee | 210/101 |
| 4,520,108 | A | 5/1985 | Yoshida et al. | |
| 4,645,647 | A | 2/1987 | Yoshida et al. | |
| 4,852,385 | A | 8/1989 | Brinkmann | |
| 4,999,305 | A | 3/1991 | Wolcott et al. | |
| 5,087,425 | A | 2/1992 | Flossdorf et al. | |
| 5,156,814 | A | 10/1992 | Fielden et al. | |

(Continued)

OTHER PUBLICATIONS

PCT International Search Report and Written Opinion for International Application No. PCT/US2008/088665 dated Feb. 9, 2009.

(Continued)

*Primary Examiner* — Brian J Sines

(74) *Attorney, Agent, or Firm* — J. Roger Williams, Jr.; Andrews Kurth LLP

(57) ABSTRACT

Disclosed are a system and method for regulating flow in an exemplary fluidic device comprising a fluidic stream carrying a transport medium, sample and one or more reagents for analysis and synthesis of reaction products. The flow rate of the fluidic stream is maintained constant by adjusting the flow rate of transport medium to compensate for the introduction of sample and reagents. An embodiment controls the flow rate of transport medium using a pump, a back pressure regulator, and a variable-sized orifice. Single and multiple channel embodiments are disclosed.

7 Claims, 17 Drawing Sheets

U.S. PATENT DOCUMENTS

| | | | | |
|---|---|---|---|---|
| 5,180,487 | A | 1/1993 | Saito et al. | |
| 5,212,095 | A | 5/1993 | Miki et al. | |
| 5,221,521 | A | 6/1993 | Hashizume et al. | |
| 5,250,263 | A | 10/1993 | Manz | |
| 5,252,486 | A | 10/1993 | O'Lear et al. | |
| 5,284,773 | A | 2/1994 | Kulkarni et al. | |
| 5,374,396 | A | 12/1994 | Blackford et al. | |
| 5,378,332 | A | 1/1995 | Pandey | |
| 5,405,781 | A | 4/1995 | Davies et al. | |
| 5,411,708 | A | 5/1995 | Moscetta | |
| 5,509,292 | A | 4/1996 | d'Appollonia et al. | |
| 5,511,408 | A | 4/1996 | Yoshida et al. | |
| 5,573,651 | A | 11/1996 | Dasgupta et al. | |
| 5,624,846 | A | 4/1997 | Hayashibe et al. | |
| 5,639,954 | A | 6/1997 | Crothers et al. | |
| 5,695,720 | A | 12/1997 | Wade et al. | |
| 5,773,298 | A | 6/1998 | Lynggaard et al. | |
| 5,783,740 | A | 7/1998 | Tawarayama et al. | |
| 5,801,820 | A | 9/1998 | Bysouth et al. | |
| 5,804,142 | A * | 9/1998 | Ito et al. | 422/70 |
| 5,858,792 | A | 1/1999 | Fanning et al. | |
| 5,889,202 | A | 3/1999 | Alapati et al. | |
| 5,965,448 | A | 10/1999 | Katou et al. | |
| 5,966,499 | A | 10/1999 | Hinkle et al. | |
| 6,083,754 | A | 7/2000 | Sakurai et al. | |
| 6,159,426 | A | 12/2000 | Palmer et al. | |
| 6,175,409 | B1 | 1/2001 | Nielsen et al. | |
| 6,179,912 | B1 | 1/2001 | Barbera-Guillem et al. | |
| 6,203,817 | B1 | 3/2001 | Cormier et al. | |
| 6,277,641 | B1 | 8/2001 | Yager | |
| 6,315,952 | B1 | 11/2001 | Sklar et al. | |
| 6,341,520 | B1 | 1/2002 | Satoh et al. | |
| 6,350,987 | B1 | 2/2002 | Northrup et al. | |
| 6,358,745 | B2 | 3/2002 | Chalk | |
| 6,438,501 | B1 | 8/2002 | Szecsody et al. | |
| 6,454,947 | B1 | 9/2002 | Safir et al. | |
| 6,524,790 | B1 | 2/2003 | Kopf-Sill et al. | |
| 6,541,213 | B1 | 4/2003 | Weigl et al. | |
| 6,577,392 | B1 | 6/2003 | Nielsen et al. | |
| 6,690,173 | B2 | 2/2004 | Blades | |
| 6,887,429 | B1 | 5/2005 | Marshall et al. | |
| 7,081,227 | B2 | 7/2006 | Clague et al. | |
| 7,198,753 | B1 | 4/2007 | Campbell et al. | |
| 7,271,007 | B2 | 9/2007 | Weigl et al. | |
| 7,329,545 | B2 | 2/2008 | Pamula et al. | |
| 7,451,634 | B2 * | 11/2008 | Gamache et al. | 73/23.42 |
| 7,468,095 | B2 * | 12/2008 | Tipler et al. | 95/82 |
| 7,625,526 | B2 | 12/2009 | van der Brink et al. | |
| 7,704,457 | B2 | 4/2010 | Patton | |
| 7,824,471 | B2 * | 11/2010 | Gamache et al. | 95/82 |
| 7,847,246 | B2 | 12/2010 | Brekenfeld | |
| 7,850,047 | B2 | 12/2010 | Boroch et al. | |
| 7,858,372 | B2 | 12/2010 | Whalen | |
| 7,927,477 | B2 | 4/2011 | Paul et al. | |
| 7,950,296 | B2 | 5/2011 | Bade et al. | |
| 8,011,224 | B2 * | 9/2011 | Kendler et al. | 73/31.05 |
| 2001/0027918 | A1 | 10/2001 | Parce et al. | |
| 2002/0187513 | A1 | 12/2002 | Kopf-Sill et al. | |
| 2003/0136176 | A1 | 7/2003 | Ruiz | |
| 2004/0163706 | A1 | 8/2004 | Volgyesi | |
| 2004/0224325 | A1 | 11/2004 | Knapp et al. | |
| 2006/0193747 | A1 | 8/2006 | Saito et al. | |
| 2007/0292310 | A1 | 12/2007 | Gravesen | |
| 2008/0213133 | A1 | 9/2008 | Wallace et al. | |
| 2009/0034359 | A1 | 2/2009 | Cardonne et al. | |
| 2009/0068760 | A1 | 3/2009 | Nelson et al. | |
| 2010/0196205 | A1 | 8/2010 | Quinn | |

OTHER PUBLICATIONS

PCT International Preliminary Report on Patentability for International Application No. PCT/US2008/088665 dated Sep. 21, 2012.

Hartwell, Upaporn Kradtap, Review Article: Flow Injection/Sequential Injection Analysis Systems: Potential Use as Tools for Rapid Liver Diseases Biomarker Study, International Journal of Hepatology, Received Oct. 15, 2011; Accepted Dec. 17, 2011, vol. 2012, Article ID 281807, 8 pages, Hindawi Publishing Corporation, doi:10.1155/2012/281807.

OI Analytical Application Note 22350205, Advantages and Disadvantages of Using Discrete Versus FIA/SFA Technology in Automated Monitoring of Ions in Water, Presented at the 2005 Pittsburgh Conference on Analytical Chemistry and Applied Spectroscopy, Orlando, FL, Feb. 27-Mar. 4, 2005, 6 pages.

Chapter III—Automatic Analytical Methods for Environmental Monitoring and Control, pp. 287-391, Leonardo Da Vinci, Education and Culture, Environmental Pollution Monitoring, Pollution, Analysis, Legislation, Quality Assurance and Managing, Edited by Andrei Florin DĂNET, Printed by S.C. PRO ACT BIROTIC S.R.L., Copyright 2005, 2nd District, Bucharest, Romania, ISBN 973-0-03917-8, http://leonardo.unibuc.ro/products/textbook.html.

Ruzicka, Jaromir and Hansen, Elo Harald, Injec Analysis, Analytical Chemisty, Mar. 1, 2000, pp. 212 A-217 A.

* cited by examiner

SYSTEM AND METHOD FOR REGULATING FLOW IN FLUIDIC DEVICES

CROSS-REFERENCE TO RELATED APPLICATIONS

This application claims the benefit of U.S. Provisional Application No. 61/017,867 filed on 31 Dec. 2007, which is hereby incorporated by reference. This application further claims the benefit of U.S. Provisional Application No. 61/137,027 filed on 25 Jul. 2008, which is hereby incorporated by reference.

BACKGROUND OF THE INVENTION

1. Field of the Invention

This invention relates to the field of flow regulation in fluidic devices. Specifically, this invention relates to the field of flow regulation in fluidic devices used in the field of chemical synthesis and analysis.

2. Background of the Invention

Many different methods have been developed for sample preparation, chemical synthesis and chemical analysis. Typical methods include continuous flow analysis and discrete batch analysis. Continuous flow analysis includes establishing a sample pipeline to enable high sample throughput independent of the complexity of the reaction. For instance, continuous flow analysis includes the ability to perform in-line sample treatments such as distillation, digestion, dialysis and solvent extraction in addition to performing complex reactions requiring the sequential addition of multiple reagents. Continuous flow sample processing enables a pipeline to be established which requires a defined amount of time for a reaction followed by processing of one sample within a defined cycle period which is significantly shorter than the reaction time for complex reactions. The major drawbacks to continuous flow analysis include the lack of ability to program tests per sample and excessive reagent usage as they are pumped continuously during the analytical process.

Beyond the analytical difficulties with current methods, continuous flow instruments are negatively impacted by the use of peristaltic pumps to provide motive force for samples and reagents. These pumps limit the performance of continuous flow systems through the peristaltic action that is an intrinsic characteristic of peristaltic pumps. This action causes pulsations in the fluid path that may adversely affect the accurate quantification of analytes passing through the fluidic device to a sample detector. Although they are relatively inexpensive, peristaltic pumps can be problematic for common applications involving sample measurements. For example, the tubing for each of the analytical streams or channels must frequently be replaced, which requires a subsequent clean-up process. Sizing issues must also be rectified in order to achieve proper quantitative "mixing" of analyte and reagents both spatially and volumetrically. Peristaltic pumps typically have a limited number of analytical channels, which each have a limited relative volume. Furthermore, the tubing used in peristaltic pumps often fails due to collapse (i.e., loss of elasticity). This tubing failure generates uneven, or non-reproducible flows, for the different channels of analyte and/or reagents being transported.

Other pumps are also not particularly suitable for a variety of reasons. For example, replacing peristaltic pumps with syringe pumps is very expensive. Moreover, other types of air displacement pumps are not suitable replacements for peristaltic pumps, because they have problems with gas solubility (e.g., air bubbles coming out of solution in the detector) and gas compressibility in the analyte transport process.

Discrete batch analysis operates by adding only the exact amount of reagents required per test per sample, which allows for automated test selection per sample and significant reduction in reagent usage. For instance, discrete batch analysis includes minimizing sample volumes, reagent volumes, and waste generation as well as providing a higher level of automation than continuous flow analysis in test profiling per sample and automated method switching. However, discrete batch analysis has major drawbacks that include (a) decreased sample throughput or number of tests per hour since each sample reaction sequence is treated discretely or independently thereby not enabling a pipeline to be established; and (b) the inability to perform in-line sample preparation.

BRIEF SUMMARY OF EMBODIMENTS

Disclosed is a system and method of regulating the flow of a fluidic device. An exemplary fluidic device is an analytical detector, and the system and method described herein can be used to provide constant sample flow at a sample detector. The system uses one or more controllers to monitor and control the addition of transport medium, sample, and reagents to one or more analytical streams in order to maintain a constant flow of the analytical streams at one or more analytical detectors. Typically, the flow rate through the analytical stream is controlled by the controllers to properly sequence the addition of the sample and one or more reaction reagents and to permit one or more reaction processes prior to constant flow analysis by the detectors. Embodiments of the system and method provide a sample pipeline with high sample throughput independent of the complexity of the reaction, without the disadvantages of peristaltic pumps or excessively wasteful flow quantities of sample or reagent. Embodiments allow for the dynamic injection of samples and reagents into the sample pipeline on an analysis-by-analysis basis where sample and/or reagent volumes can be optimized for the specific measurement. The result embodies an automated device that, like a discrete batch analysis method, provides a high level of automation, minimizes sample volumes, reagent volumes, and waste generation, while maintaining the continuous flow sample pipeline and throughput capabilities of continuous flow analysis.

An exemplary implementation of the system comprises one or more analytical streams flowing through a pumping system and flow control module, a sample introduction module, a sample reaction module, and a sample detection module. An exemplary pumping system and flow control module comprise a pump, a back pressure regulator and one or more fluidic flow controllers. The pump draws transport medium from a reservoir and directs it to the one or more analytical streams. The back pressure regulator positioned downstream of the pump maintains a constant pressure of the transport medium to each of the analytical streams. The fluidic flow controller maintains a constant flow rate of transport medium in each of the analytical streams. In one implementation of the system, the sample introduction module comprises a syringe pump and an isolation loop. In an embodiment, the sample reaction module includes inlets for the introduction of reagents into the analytical streams and one or more reaction devices, some of which may be user-configurable. The pumping system and flow control module reduce the flow rate of transport medium to compensate for the introduction of sample and reagents into the analytical streams, thereby maintaining a constant flow at the sample detection module.

Also disclosed is a system comprising one or more fluidic carrier streams, a first injection means for injecting a first substance into a carrier stream to make a first stream, a second injection means for injecting a second substance into the first stream to make a second stream, and a flow regulator that maintains the second stream at a constant flow rate by adjusting the flow rate of the carrier stream to compensate for the introduction of the first and second substances. An embodiment of the system comprises a fluidic flow controller comprising a orifice.

Also disclosed is an embodiment of a system for intermittent introduction of sample and reagent(s) into a continuously flowing carrier stream. The system includes a means to propel the carrier stream by a non-pulsatile mechanism, a sample injection valve to introduce the sample into the carrier stream and a means to introduce discrete aliquots of reagents into the continuously flowing stream at pre-programmed intervals. The non-pulsatile characteristic of the carrier stream pumping mechanism of the system allows the location of the sample within the carrier stream to be known at any time following sample introduction into the carrier stream. At least one reagent is added to the sample in the carrier stream when the sample carrier stream is disposed at a desired location in the sample and reagent addition system.

Also disclosed is a system comprising a constant flow pump to deliver a transport medium to a manifold, a back pressure regulator that maintains constant pressure at the manifold, transport medium flowing through the manifold via a flow element, and a valve in the flow element to control the flow of transport medium thereby creating an analytical stream. The system also includes a syringe pump that injects a volume of sample into the analytical stream downstream of the valve, at least one reagent inlet for injecting a reagent into the analytical stream, at least one mixing volume downstream of the reagent inlet, the mixing volume arranged and designed to permit a reaction between said reagent and said sample to create a reaction product, a detector to analyze the reaction product, and a flow controller that controls the valve, the syringe pump, and the reagent injection such that a constant flow of the analytical stream containing the reaction product is delivered to the detector.

Also disclosed is a method for regulating flow in a fluidic device comprising delivering a fluidic carrier stream at a substantially constant flow rate, introducing first and second substances into the carrier stream to make a second stream having a second stream flow rate, and regulating the carrier stream flow rate so that the second stream flow rate remains substantially constant.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
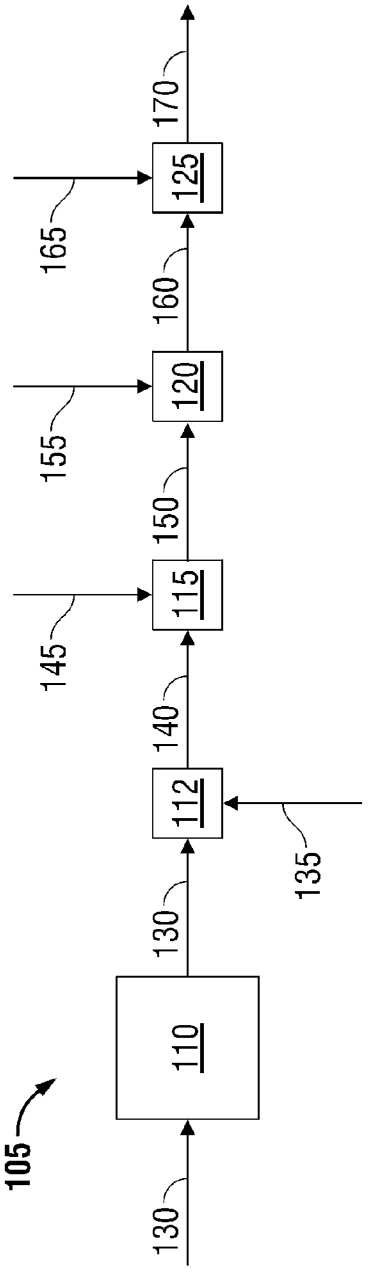
FIG. 1 illustrates an embodiment of a sample and reagent addition process having distributed flow.

FIG. 1 illustrates a process and system for regulating flow in an exemplary fluidic device comprising a sample and reagent addition process 105 including pump 110, sample addition point 112, and reagent addition points 115, 120 and 125. Pump 110 may include any pump suitable for pumping a liquid provided that it is sufficiently accurate and precise in operation to position the sample zone in both a known and reproducible fashion to enable the overlay or merging of subsequent reagent aliquots into the sample zone. In the preferred embodiment, pump 110 includes a non-peristaltic non-pulsatile pump with high accuracy and precision in terms of flow rate against variable backpressures. An exemplary pump 110 is an electronically adjustable rotary pump. It is to be understood that sample and reagent addition process 105 is not limited to three reagent addition points 115, 120 and 125 but may have more or less than such three reagent addition points.

As shown in FIG. 1, sample and reagent addition process 105 includes carrier stream 130. Carrier stream 130 includes any fluid suitable for transport of sample 135 and reagents 145, 155 and 165. In an embodiment, carrier stream 130 includes a fluid that is non-reactive with sample 135 and reagents 145, 155 and 165. In some embodiments, carrier stream 130 is deionized water. In some embodiments, carrier stream 130 is continuously pumped through a fluidic conduit using pump 110, which in some embodiments is a non-pulsatile pump. The fluidic conduit may include any suitable piping or tubing having any suitable bore diameter. In an embodiment, the bore has a diameter from about 0.1 mm to about 1.0 mm. In an embodiment, sample 135 is introduced to carrier stream 130 downstream of pump 110 at sample addition point 112 to create a sample zone within the carrier stream 140. In an embodiment, reagent addition is made at reagent addition point 115 concurrent with the sample carrier stream 140 passing reagent addition point 115. At reagent addition point 115, reagent 145 may be added to sample carrier stream 140 to provide stream 150. Stream 150 may then be provided to reagent addition point 120 at which reagent 155 may be added to provide stream 160. Stream 160 may be provided to reagent addition point 125 at which reagent 165 may be added to provide reaction product 170. In some embodiments, sample and reagent addition process 105 is automatically controlled such as by a computer system.

As further shown in FIG. 1, sample 135 may be added to sample addition point 112, and reagents 145, 155 and 165 may be introduced to the respective reagent addition points 115, 120 and 125 by any suitable method and device. Examples of such suitable methods include bolus injection or by continuous addition. In an embodiment, a suitable method is continuous addition. In such an embodiment, the addition point (e.g., sample addition point 112 or reagent addition points 115, 120 or 125) includes a tee fitting. In alternative embodiments, the addition point includes a valve or pump to enable non-continuous, intermittent and precise reagent introduction into the sample carrier stream. In some embodiments, the valve is a two-position valve with a load position and an injection position. In some embodiments, the pump is capable of rapid on-off cycling with no significant hysteresis.

In alternative embodiments, any of streams 130, 140, 150, 160 and 170 may be segmented with an alternative phase. The alternative phase may be gas or liquid. In some alternative embodiments, segmentation may be performed at any position along the flow path (e.g., before or after sample introduction). In other alternative embodiments, any of streams 130, 140, 150, 160 and 170 may be de-segmented at any position along the flow path. In addition, alternative flow regimes may be provided at any position along the flow path for any streams 130, 140, 150, 160 and 170. For instance, alternative flow regimes such as, without limitation, bolus flow, laminar flow, turbulent flow, or any combinations thereof may be provided at any position along the flow path.

Sample 135 and reagents 145, 155 and 165 may be added at any angle to the respective stream flow. In an embodiment, sample 135 and reagents 145, 155 and 165 are added at about a 90° angle to the flow path of the respective stream.

It is to be understood that as the sample proceeds through the fluidic conduit, the characteristics of pump 110 may enable the location of the sample zone within the reaction conduits to be known at any given time. For instance, the continuous and non-pulsatile flow allows the sample location within sample and reagent addition process 105 to be known at any time, which allows the proper time at which to add a reagent to be known. It is to be further understood that sample and reagent addition process 105 provides a pulsed or intermittent addition of liquids or gases to a carrier stream (e.g., carrier stream 130) through an addition point (e.g., either a valve or a tee fitting). In such embodiments, successive liquid boluses may be overlaid onto an existing zone. For instance, such an overlay may allow reagent addition in precise quantities and in sufficient volumes for a particular reaction. In addition, the sample/carrier stream (e.g., sample carrier stream 140) may also encounter a solid phase such as an ion exchange, extraction, reduction or oxidation column, a wet or diffusion-based distillation device, a phase combination device, a phase separation device, a heat-based and/or a light-based digestion device and a dialysis device.

It is to be further understood that sample and reagent addition process 105 includes a mixing stage after each addition point. In some embodiments, the distance between the addition points along the flow path is selected to allow a desired mixing of the reagents and sample.

Figure 2:
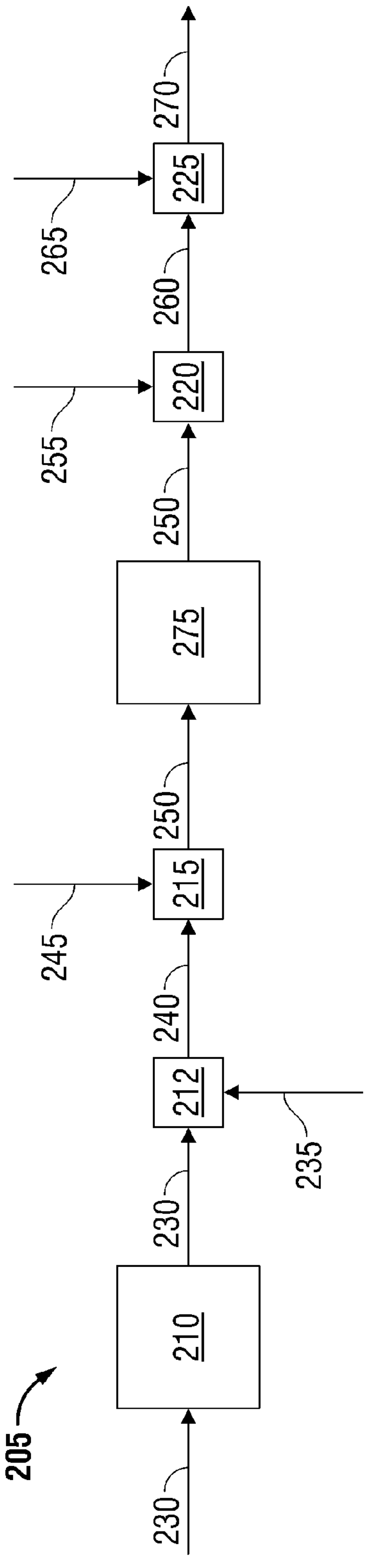
FIG. 2 illustrates an embodiment of the process of FIG. 1 having a downstream pump.

In an alternative embodiment, the exemplary sample and reagent addition process 105 includes at least one additional pump downstream of pump 110. FIG. 2 illustrates an embodiment in which an exemplary sample and reagent addition process 205 includes pump 275 downstream of pump 210 and upstream of reagent addition point 220. Sample and reagent addition process 205 may also or alternatively include a pump upstream of reagent addition points 215 and/or 225.

In some embodiments, sample and reagent addition process 205 includes a method comprised of a carrier stream (or alternatively a propulsion stream) driven forwards and backwards in fluidic conduits by a highly precise pump and one or more additional pumps downstream, operating independently or in series. Such pumps allow for the addition of chemicals (e.g., either continuously or intermittently) to achieve a goal of a selected technique. Without limitation, such techniques my include preparation of a sample using distillation, digestion, dilution, dialysis, solvent extraction, ion exchange, field flow fractionation and derivatization of selected analytes contained in a sample to generate a reaction product that may be subsequently delivered to a detector. Examples of detectors include spectrophotometers and electrochemical detectors for quantification and small scale chemical synthesis.

Sample and reagent addition processes 105, 205 provide a method for the purpose of chemical synthesis, including, but not limited to reaction products quantifiable for analytical purposes, manipulation of cells and bacteria, manipulation of multi-phase streams, ion exchange for both sample preparation and separation applications and field flow fractionation for either sample preparation or separation.

To further illustrate various illustrative embodiments of the present invention, the following examples are provided.

Example

An example application of sample and reagent addition process 105 is in the determination of nitrate in water samples. In preparation for sample processing, a carrier stream was aspirated into a syringe through a valve aligned with a reservoir of deionized water. The valve was then switched to place the syringe in-line with the primary fluidic conduit, and the carrier was pumped downstream through the entire fluidic conduit and into a flow cell where a water baseline was established. This apparatus corresponded with pump 110 in FIG. 1.

Once the water baseline was established, the sample was injected into the carrier stream at sample addition point 112 in FIG. 1. Subsequently, a quantity, of ammonium chloride (R1) was pulsed into the carrier stream on top of the sample zone in the carrier as it passed reagent addition point 115 in FIG. 1 and pumped into a mixing device and a reaction device. The carrier/R1 combination was then pumped through a conduit coated with cadmium to reduce nitrate to nitrate corresponding to stream 150 in FIG. 1. Upon exiting from the cadmium reduction section, a quantity of naphthyltheylenediamine dihydrochloride (R2) was pulsed into the sample/ammonium chloride stream as such combination passed the R2 inlet at reagent addition point 120 in FIG. 1, which was then directed through a second mixing and reaction device for the purpose of derivatizing the nitrate to generate a colored reaction product. In this example, a third reagent was not required to be added at reagent addition point 125. The absorbance of the reaction product was read at 520 nm to establish a reagent baseline. In the absence of the addition of a sample zone, such mixture yielded a reagent blank.

Once the reagent baseline (blank) was established, a quantity of sample was introduced into the carrier, and R1 was pulsed into the sample zone in the carrier followed by mixing and reaction. The buffered sample was then pumped through the cadmium reduction conduit followed by addition of R2 to the buffered sample zone and mixing and reaction of R2 with the buffered sample zone. The reaction product was pumped into the absorbance detector flow cell where a transient signal was generated as the transmittance of the light in the flow path was decreased resulting in a transient peak, which represented the distribution of the sample/R1/R2 zones in the carrier and the height and area of which were directly proportional to the quantity of nitrate and nitrate present in the original sample based on a calibration curve.

An embodiment of a system and method for regulating flow to an fluidic device utilizes a electronic controller to integrate one or more fluidic flow controllers and any number of substance introducers (e.g., injectors) based on an algorithm that ensures the total flow rate remains nearly or substantially constant during the injection of samples or reagents in to the flow stream. The controller (a personal computer or imbedded microprocessor properly programmed) controls the independent device timing to maintain the final flow rate at the detector. This front end flow control allows the sensitive and expensive flow sensor in the fluidic flow controller (FFC) to be located where it is only exposed to inert transport medium avoiding corrosive reagents and the possibility of plugging from sample particulates.

The flow rate in a channel can be described generally by the equation:

$$F_{total}F_{TM}F_{inj\ 1}+F_{inj\ 2}+F_{inj\ 3}\ldots+F_{inj\ n} \quad (1)$$

Where:

$$F_{total}\text{ (or Total Flow)=Total flow rate of the system} \quad (2)$$

$$F_{TM}\text{=Flow rate of the transport medium} \quad (3)$$

$$F_{inj\ j}\text{=the flow rate added by injector } j \text{ (for } j\text{=1 to } n) \quad (4)$$

The basic equation preferably ignores the detail of the acceleration/deceleration profiles of the injectors and the FFC because it is assumed in an embodiment that the acceleration/deceleration profile of the FFC will be the inverse of the acceleration/deceleration profile of the injectors.

Figure 3:
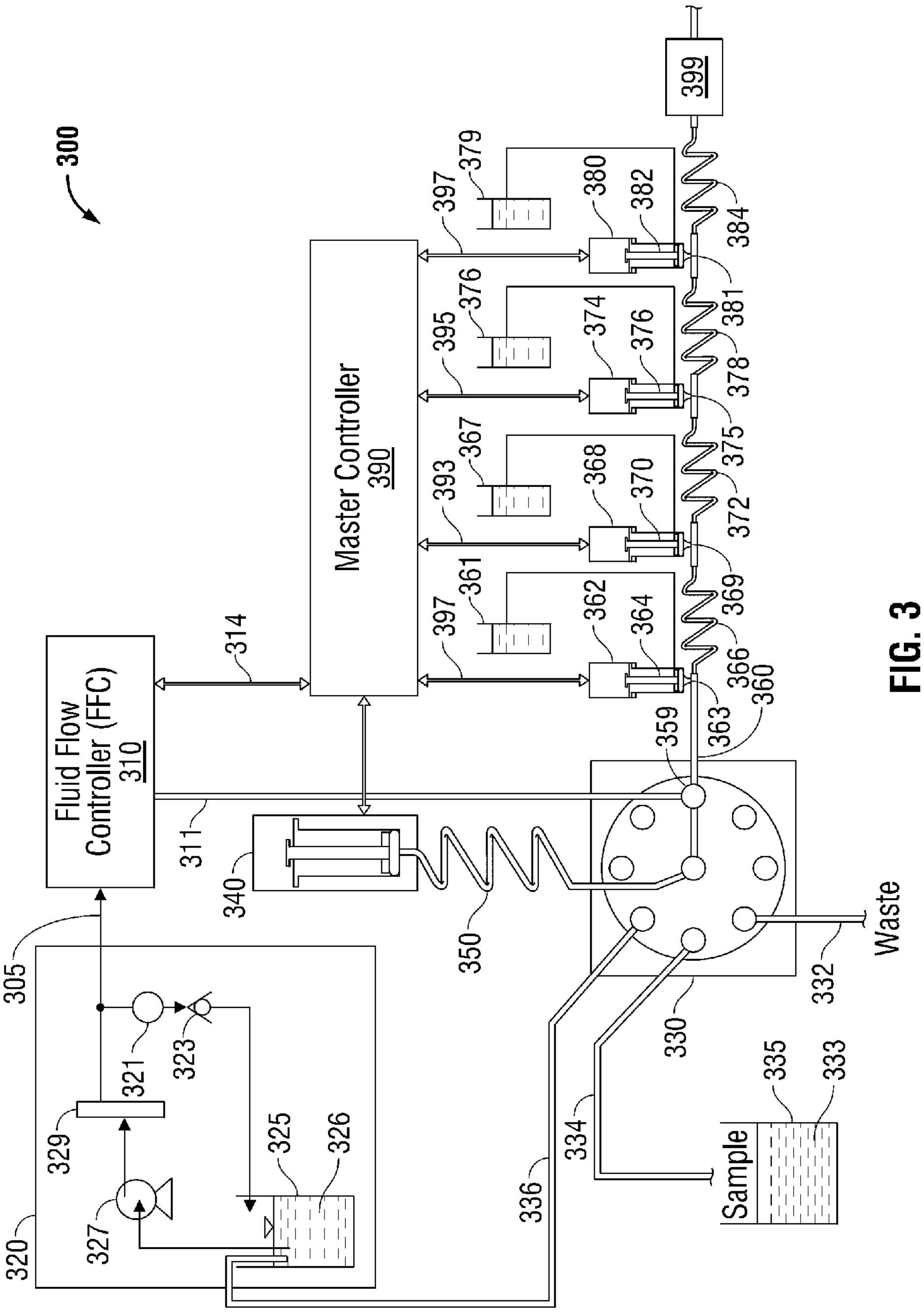
FIG. 3 illustrates an embodiment of a system for regulating flow in a fluidic device.

FIG. 3 illustrates an embodiment of a system 300 for regulating flow in a fluidic device having a single channel. Preferably the total flow rate of the system ($F_{total}$) remains constant or substantially constant throughout the processing of samples. $F_{target}$ refers to the target total flow rate. An exemplary target total flow rate in an embodiment is 2000 μL/minute. Embodiments of system 300 can accommodate greater or lesser volumes and flow rates. Preferably system 300 can accommodate flow rates associated with analysis in the range of nanoliters to centiliters per minute.

System 300 provides a two-part pump system which includes a constant pressure system 320 and a fluidic flow controller (FFC) 310 which utilizes a voltage-controlled orifice (VCO) to vary flow. The combination of constant pressure system 320 and FFC 310 perform the function of pump 110 illustrated in FIGS. 1 and 2.

As illustrated in FIG. 3, constant pressure system 320 preferably comprises a pump 327, a filter element 329, a transport conduit 305, a pressure sensor 321, a back pressure regulator 323, and a reservoir 325 containing a transport medium 326. Pump 327 draws transport medium 326 from reservoir 325 and directs it to a transport conduit 305, at a flow rate that exceeds the total flow requirement of the stream. Pump 327 is a pump such as an electronically adjustable rotary pump but may be another form of pump, preferably non-peristaltic or any other suitable device known to those of skill in the art that can provide constant pressure and adequate flow to transport conduit 305. The transport medium 326 is preferably a highly purified water (i.e., de-ionized water), however, alternative transport media may include perfluorinated polyether (PFPE) (i.e., Krytox® by Dupont), multiply-alkylated cyclopentanes (i.e., Pennzane® by Royal Dutch Shell), or any other highly hydrophobic fluid. Pump 327 preferably maintains a flow rate across filter element 329 that is positioned between the pump 327 and transport conduit 305. Filter 329 eliminates any particulates which may interfere with the operation of the variable orifice or contribute error to the analysis. Filter 329 can be any type of particulate filter, preferably in the 5 micron filtering range.

Back pressure regulator 323 preferably is disposed in a side stream positioned downstream of the pump 327 between the filter element 329 and transport conduit 305. The back pressure regulator 323 maintains the transport medium at a constant pressure in transport conduit 305 and minimizes any pulsation or other flow irregularities from pump 327. In an embodiment, the preferred constant pressure is 20 psig, and the back pressure regulator 323 preferably maintains the pressure at 20 psig such that the pressure to the transport conduit 305 is also maintained at 20 psig. Back pressure regulator 323 preferably operates by permitting the flow of transport medium therethrough at a varying flow rate to maintain the back pressure at a desired level. Any excess transport medium 326 flowing through back pressure regulator 323 is returned to the reservoir 325 for reuse. The output signal from pressure sensor 321, positioned between the filter element 329 and the back pressure regulator 329, is used to verify performance of pump 327 either manually or through automatic feedback control. Preferably pressure sensor 321 is used to determine the supply side pressure in transport conduit 305. As is well known in the art, the differential pressure between the supply side pressure in transport conduit 305 and the flow side conduit 311 may be used to determine the flow rate in flow side conduit 311.

Figure 4:
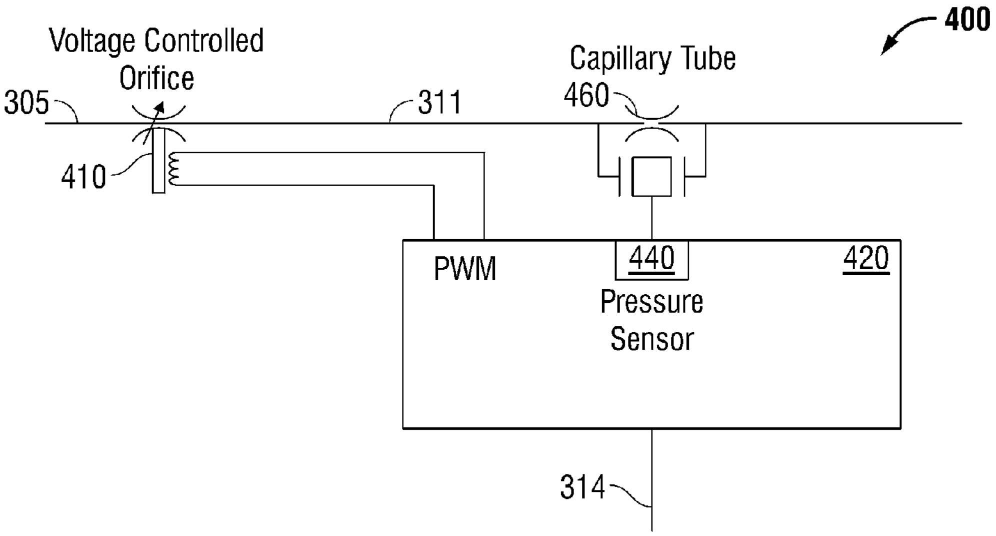
FIG. 4 illustrates an exemplary embodiment of a fluidic flow controller.

FIG. 4 illustrates an embodiment of FFC 310 including a Voltage Controlled Orifice (VCO) 410, controller 420, capillary tube 430, and differential pressure sensor 440. The pump 327 and back flow regulator 323 of exemplary constant pressure system 320 provide constant pressure for the FFC 310 which varies the size of the VCO 410 at a fixed pressure to generate a particular flow. Additionally the back pressure regulator 323 dampens any pulsations generated by the pump 327 thereby enhancing control by the FFC 310. In this case the VCO 410 separates transport conduit 305 and flow side conduit 311, so varying the orifice size with constant pressure varies the flow rate in flow side conduit 311. In an alternative embodiment, the size of the orifice in VCO is fixed and pump 327 can deliver controllably variable pressure (for example, under the control of controller 420. In this alternative embodiment, controller 420 can regulate the flow rate through the fixed orifice by controllably varying the pressure through the fixed orifice. As described in more detail below, transport medium 326 in flow side conduit 311 provides a carrier stream which in an embodiment will be combined with sample and reagent for analysis by a downstream detector or synthesis.

Controller 420 adjusts VCO 410 to regulate the flow of transport medium 326 from transport conduit 305 into flow side conduit 311. Additions of sample or reagents increase or decrease the flow rate in analytical stream 360, and in an embodiment master controller 390 directs controller 420 to adjust VCO 410 to compensate for the addition of sample or reagent to ensure that the flow rate in analytical stream 360 remains constant or substantially constant. The flow rate of transport medium 326 through FFC 310 is monitored by measuring the differential pressure across capillary tube 460. In another embodiment a single pressure sensor positioned to measure the pressure in flow side conduit 311 could be used in concert with pressure sensor 321 positioned to measure the pressure in transport conduit 305 to determine the flow rate in conduit 311. The differential pressure across capillary tube 460 is sensed by differential pressure sensor 440, which preferably includes an analog-digital converter (not numbered). The output from pressure sensor 440 is input into controller 420 which controls the voltage applied to VCO 410 located upstream from capillary tube 460. In an embodiment the signal from pressure sensor 440 is filtered to remove interference. VCOs (or equivalent variable-sized orifices), fixed orifice elements, capillary tubes and pressure sensors are well-known and readily available to those of skill in the art.

Controller 420 preferably includes a programmable interface controller including a CPU, input/output ports and means for controlling same such as a USART, on-board data space or RAM, memory, and code space or control software, preferably implemented an EPROM, ROM or Flash ROM, that includes instruction codes which when processed by the CPU cause controller 420 to perform the algorithms and methods described herein. An exemplary programmable interface controller is the PIC 18F4520 made by MicroChip Technology, which can be adapted for use in embodiments described herein with development tools such as MPLAB. In an embodiment controller 420 uses a loop control feedback process, preferably a proportional-integral-derivative (PID) control process based on flow rate readings obtained through capillary tube 430 and pressure sensor 440 to change the voltage supplied to VCO 410. Controller 420 preferably uses pulse width modulation (PWM) to control VCO 410. In an embodiment controller 420 includes a control line to control pump 327.

In an embodiment FFC 310 is a slave in a master-slave configuration with master controller 390 and controller 420 receives control input via control line 314 from master controller 390. Preferably master controller 390 provides a control signal indicating the desired flow rate, or alternatively a desired change in flow rate, for transport medium 326 in flow side conduit 311. Controller 420 responds to the control signal from control line 314 by adjusting the size of the orifice in VCO 410 to adjust the flow rate of transport medium 326 in flow side conduit 311. The control signal to FFC 310 may be analog, for example a voltage between 0 and 5 volts dc, or a command issued over a serial link. In an alternative embodiment, controller 420 is integrated with master controller 390, through, for example, common hardware resources and/or common control software. In another alternative embodiment, controller 420 receives control information directly from pump 340 and injectors 364, 370, 376 and 382 by, for example, a serial link or an analog signal line.

Exemplary system 300 includes a valve 330 to enable controlled introduction of fluid into analytical stream 360. Valve 330 preferably is a multi-port valve that provides ports to accommodate at least at least one analytical stream along with sample, transport media and waste. In an embodiment valve 330 is an 8-port rotary valve such as, preferably, a Cavro XL 3000, which allows for up to five analytical streams (only one of which is illustrated in exemplary system 300 in FIG. 3). Valve 330 includes output ports connected to analytical stream 360 and waste disposal line 332. Valve 330 includes input ports connected to transport line 336 carrying transport medium from reservoir 325 and sample line 334 carrying sample 333 from sample reservoir 335. In an embodiment the motive force for moving fluid through valve 330 is provided by pump 340 connected via isolation loop 350 to a common port (e.g., center port) of valve 330. Flow side conduit 311 carries transport medium 326 through one arm of "Tee" 359 connected to a port of the valve 330 and out the other arm into analytical stream 360. Sample 333 preferably is introduced (e.g., from isolation loop 350) via valve 330 into another arm of Tee 359 connected to valve 330, so that a combined stream of sample 333 and transport medium 326 flows out of Tee 359 into analytical conduit 360. Preferably valve 330 is controlled by master controller 390.

Those of ordinary skill in the art will appreciate that other types and configurations of valves also can be used in embodiments. An alternative embodiment of a suitable valve is described below and illustrated in FIGS. 15A-E.

Pump 340 in an embodiment is a syringe pump although other types of pumps, preferably a non-peristaltic pump such as a rotary pump with an injection valve, may be substituted for pump 340. Pump 340 draws a sample from a sample source 335 via sample line 334 through valve 330 and into the isolation loop 350. Pump 340 preferably is controlled by master controller 390. An exemplary pump 340 can be obtained as an assembly with the Cavro XL 3000.

Isolation loop 350 prevents the entry of the sample into the cavity of the pump 340, thereby preventing the transference of one sample into another (i.e., carrier-over). Isolation loop 350 allows for filling pump 340 with inert transport media while having the volume capacity in loop 350 to hold a required quantity of sample without sample ever contaminating the syringe. In the single channel system illustrated in FIG. 3, isolation loop 350 preferably has sufficient volume to hold at least the minimum volume of sample required to conduct one complete cycle of reactions. In an embodiment having multiple channels (such as the system illustrated in FIGS. 12-13), isolation loop 350 preferably has sufficient volume to hold at least the minimum volume of sample required to conduct one complete cycle of reactions for all channels, so that the syringe pump 340 can cycle through each channel and introduce a required quantity of sample into each channel without having to aspirate additional sample.

When exemplary system 300 is initialized, valve 330 is rotated to the waste port and the syringe of pump 340 is driven to the full dispense position. The valve 330 then rotates to the transport medium position and pump 340 draws transport medium 326 from reservoir 325 via line 336 through a port of valve 330 and into pump 340 and isolation loop 350, Valve 330 is again rotated to the waste position and transport medium is expelled through waste line 332 until all air is removed from isolation loop 350. The pump is mounted vertically to ensure any air is displaced prior to liquids, and system 300 is ready to operate.

When priming a sample, valve 330 is rotated to receive sample 333 via sample line 334 and the syringe in pump 340 is driven to aspirate the appropriate volume of sample 333 to fill the dead volume of the sample tubing 334 plus a predetermined excess. Valve 330 is rotated to the waste port and the syringe is driven to full dispense position to expel the excess sample. Valve 330 then rotates back to the sample position and pump 340 pulls a volume of sample 333 into isolation loop 350. Valve 330 rotates to an analysis stream position where pump 340 dispenses the appropriate volume of sample 333 into Tee 359 where it is injected into the transport medium flowing therethrough from flow side conduit 311 and into analytical stream 360. After injection, valve 330 returns to the waste port where any excess sample and a portion of the transport medium are expelled to waste.

As further shown in FIG. 3, the arrangement of system 300 permits the isolation loop 350 to be flushed or rinsed between samples. When the pump 340 is filled with the transport medium from reservoir 326, the isolation loop 350 is flushed by the transport medium flow from the pump 340 when the valve 330 is selected to direct the transport medium flow to the waste disposal line 332. By appropriately cycling pump 340 and the position of the multi-port valve 330, sample 333 or transport medium 326 can be pulled from the sample reservoir 335 or transport medium reservoir 325, respectively, and either introduced into analytical stream 360 or sent to the waste disposal line 332.

In an alternative embodiment, one or more sensors (unnumbered) may be positioned within the waste disposal line 332 to sense the presence (or lack thereof) of fluid therein, and thus minimize the wasteful consumption of sample due to the overloading of the waste disposal line 1250. Preferably such sensors include a conductivity sensor, however, other types of sensors may be used including, but not limited to, optical sensors, capacitance sensors, or pressure sensors. An autosampler probe (unnumbered), well known to those of skill in the art, may be employed in conjunction with the sample line 334 to automate and speed up the analysis of multiple samples.

Exemplary system 300 comprises one or more reagent inlets, preferably four reagent inlets 363, 369, 375, 381, positioned along the length of analytical stream 360 and one or more mixing loops/volumes 366, 372, 378, 384. One or more reagents are introduced into analytical stream 360 at the proper time, place, and flow rate through reagent inlets 363, 369, 375, 381 to react with sample 331 and each other. The flow rate of transport medium 326 in flow side conduit 311 is adjusted inversely in relation to the added flow of the sample and the reagents into analytical stream 360 to maintain a constant or substantially constant flow rate. Although exemplary system 300 illustrates sample being introduced into analytical stream 360 upstream of reagents, it should be understood that in an alternative embodiment one or more reagents can be introduced into analytical stream prior to the introduction therein of any sample.

System 300 includes mixing loops/volumes 366, 372, 378, 384 as reaction devices to enable multiple different reaction sequences. In an embodiment the user can configure one or more of the mixing loops/volumes 366, 372, 378, 384 into any desired reaction device by substituting piping or tubing having any desired configuration, including length (for example, from fractions of an inch to several meters), bore (preferably in a range from mictron sizes to multiple millimeters), shape (for example, straight, serpentine, or undulated), and material (e.g., teflon or polymers, quartz or other glassy type materials, or metallic tubing), as called for by the reactions anticipated to occur within the piping or tubing. Exemplary reaction devices include analytical loops, delay loops, heated or cooled zones, catalytic zones or other reaction support devices.

System 300 provides means to introduce one or more reagents in analytical stream 360 and to control the timing and amount of introduction of reagents. System 300 as shown in FIG. 3 includes injectors 364, 370, 376 and 382 to introduce reagents through inlets 363, 369, 375, 381 into analytical stream 360. Injectors 364, 370, 376 and 382 in FIG. 3 are actuated via injector motor drivers 362, 368, 374, and 382. Injector motor drivers 362, 368, 374, and 382 are controlled by Master Controller 390. FIG. 3 also shows reagent reservoirs 361, 367, 373, and 379 coupled to injectors 364, 370, 376 and 382. A preferred injector and injector motor is the Variable volume pump LPVX0502150B available from Lee Company. Those of ordinary skill in the art will recognize that other means can be used to add or introduce reagents to analytical stream 360, including, for example, miniature solenoid pump LPLA1210550L available from Lee Company.

Master controller 390 in exemplary system 300 controls pump 340, valve 330, injector motor drivers 362, 368, 374 and 380 and, via FFC 310, the flow rate of the transport medium in analytical streams 311 and 360 as described below in connection with FIGS. 5-9. In an embodiment, master controller 390 is implemented on a computer, such as a personal computer or workstation, comprising at least a CPU, input/output ports and means for controlling same such as a USART, memory, including RAM, and persistent storage for storing operating instructions and data. Master controller 390 includes software, code and instructions operative to implement the control functions and methods described herein in a manner familiar to those of ordinary skill in the art. Preferably master controller 390 also includes input devices (such as a mouse and a keyboard) and output devices (such as a monitor) and user interface software to enable user configuration and control of different components and parameters of system 300 and monitoring and display of reservoir levels of transport medium 326, sample 331 and reagents in reagent reservoirs 361, 367, 373 and 379, and monitoring and display of the operation and status of the different components of system 300, including pump 340, valve 330, FFC 310, injectors and injector motors 362, 364, 368, 370, 374, 376, 380, 382, and detector 399. In an embodiment, FFC 310 us separate and not integrated with master controller 390. In an alternative embodiment FFC 310 is integrated with master controller 390. For example, the software instructions implementing the control processes performed by controller 420 of FFC 310 can be implemented on master controller 390, and/or controller 420 of FFC 310 may share hardware resources such as CPU, USART or other I/O control, system clock power supply, data or control bus, or RAM.

Master controller 390 preferably includes control software to control valve 330, the injection devices, i.e., the reagent injector motors 362, 368, 374, 380 and pump 340, and FFC 310. The timing of introduction of reagents or sample can be controlled by master controller 390 based on elapsed time. Suppose, for example, it is desired to control injector 382 to introduce a reagent through inlet 381 into analytical stream 360 to react with sample 331. Because the flow rate of analytical stream 360 is constant or substantially constant and the relevant distance (e.g., between the point wherein sample 331 is introduced into analytical stream 360 and 381) is known, the elapsed time when sample 331 will flow by inlet 381 can be determined and the control software can initiate injector motor 380 at the elapsed time. Alternatively, the timing of introduction of reagent can be determined based on detection of sample or another reaction product in analytical stream 360. In an embodiment, a conductivity sensor can be employed to detect the presence of sample by measuring the conductivity of analytical stream 360 around inlet 381, so that when the conductivity sensor detects a change in conductivity indicating presence of sample, it can trigger injection motor 380 or, preferably, set a flag to trigger injection motor 380 during the next system timer interrupt. It is to be understood that this discussion focusing on injector 382, inlet 381 and injection motor 380 is explanatory and the same principles apply to the other injectors in system 300.

In an embodiment the injection rates and volumes for each injection device are preset to a constant value. When the control software encounters an injection event at injector 382 during servicing of a system timer interrupt, it will signal injector motor 380 to introduce a quantity of reagent corresponding to the preset constant value for the injection rate and volume and the system timer frequency. At the same time, preferably during the same system timer interrupt service routine, the control software will signal FFC 310, via control line 314, to reduce the flow rate of transport medium 326 in flow-side conduit 311 by an amount corresponding to the volume of reagent introduced into analytical stream 360 by injector 382.

In an embodiment, the control software for master controller 390 can employ different injection rates and volumes for each injection device. Preferably the control software will maintain for each injection device a queue containing sequentially-accessed values corresponding to a desired injection rate and volume for each system timer cycle, and these values can be preset or dynamically controlled via master controller software. Preferably a separate queue is used for each sample and reagent injector to allow the controller 390 to compensate for overlapping injections. In an embodiment, pump 340 is adapted to supply sample to multiple channels, i.e., multiple parallel analytical streams, and in that embodiment the control software preferably maintains a separate sample injector queue for each channel.

System 300 also includes a detector 399. Exemplary detectors 399 are an oscilloscope, a photometric detector, a spectrophotometer, an electrochemical detector, and any other form of detector known to those of skill in the art suitable for use in analysis, quantification and small-scale chemical synthesis.

One or more reaction sequences, chemistries or processes may be performed in analytical stream 360 to convert the sample into a reaction product (i.e., analyte) that permits quantification and characterization by detector 399. For example, electrochemical cells, ion exchange, oxidation or reduction chemistries, ultraviolet sources, heat sources, active metal surfaces, catalytic materials, phase separation elements, and digestions may be employed to produce the desired reaction product for quantification and characterization by detector 399. Furthermore, the analytical stream 360 may be configured to have one or more samples present at any given time in a serial arrangement (not shown) along the length of the analytical stream 360. After analytical stream 360 has been analyzed at the detector 399 of system 300, the contents of analytical stream 360 are expelled to waste.

In an alternative embodiment, instead of dispensing the contents of analytical stream 360 to waste, the contents of analytical stream 360 can be recycled to undergo another cycle of reaction processes. This alternative embodiment includes a recycling conduit (unnumbered) with one end connected to a recycling valve (unnumbered) and the other end connected to analytical stream 360 via valve 330 or an injector 364, 370, 376, 382. The recycling valve preferably is connected to analytical stream between mixing volume 384 and detector 399. Preferably master controller 390 controls the recycling valve to recycle the contents of analytical stream 360 and to send the recycled contents of analytical stream 360 to detector 399 after the desired number of cycles.

FIGS. 5 through 9 illustrate different stages of exemplary control algorithms implemented by FFC 310 and Master Controller 390 in connection with the operation of system 300 utilizing 4 reagents.

Figure 5:
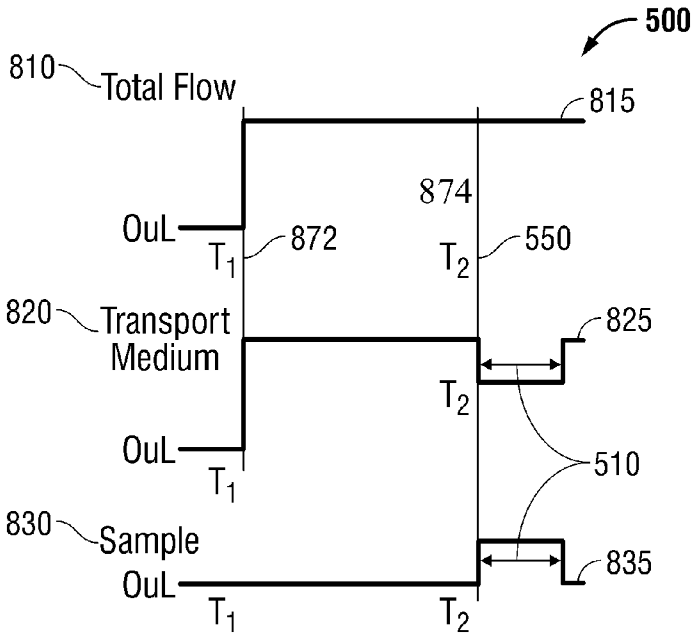
FIG. 5 illustrates exemplary flow rates in a system for regulating flow in a fluidic device with a single flow stream comprising a transport medium and a sample.

FIG. 5 provides a timing diagram 500 showing flow rates at time $T_2$ 874. Depicted are flow rates 825 for transport medium 820, 815 for Total Flow 810, and 835 for Sample 830. When the system is up to the required flow and stable, sample 830 is injected into the flow stream at $T_2$ 874, as shown by the increase in flow rate 835 of Sample 830 during a time interval 510. During the injection of sample 830, FCC 310 adjusts the flow rate of transport medium 820 to maintain the Total Flow at the target total flow rate 809. When the sample 830 is injected at $T_2$ 874, $F_{inj\ 1}$ will go from 0 μL/minute to some number less than the target total flow rate 809. FCC 310 then will reduce the flow rate 825 of transport medium 820 to a flow rate equal to $F_{total}-F_{inj\ 1}$. When the injector ceases to inject Sample 830, i.e. when $F_{inj\ 1}$ is taken down to 0 μL/minute at the end of interval 510, FCC 310 increases the flow rate 825 of transport medium 820 to bring Total Flow 815 back to the target total flow rate 809.

Figure 6:
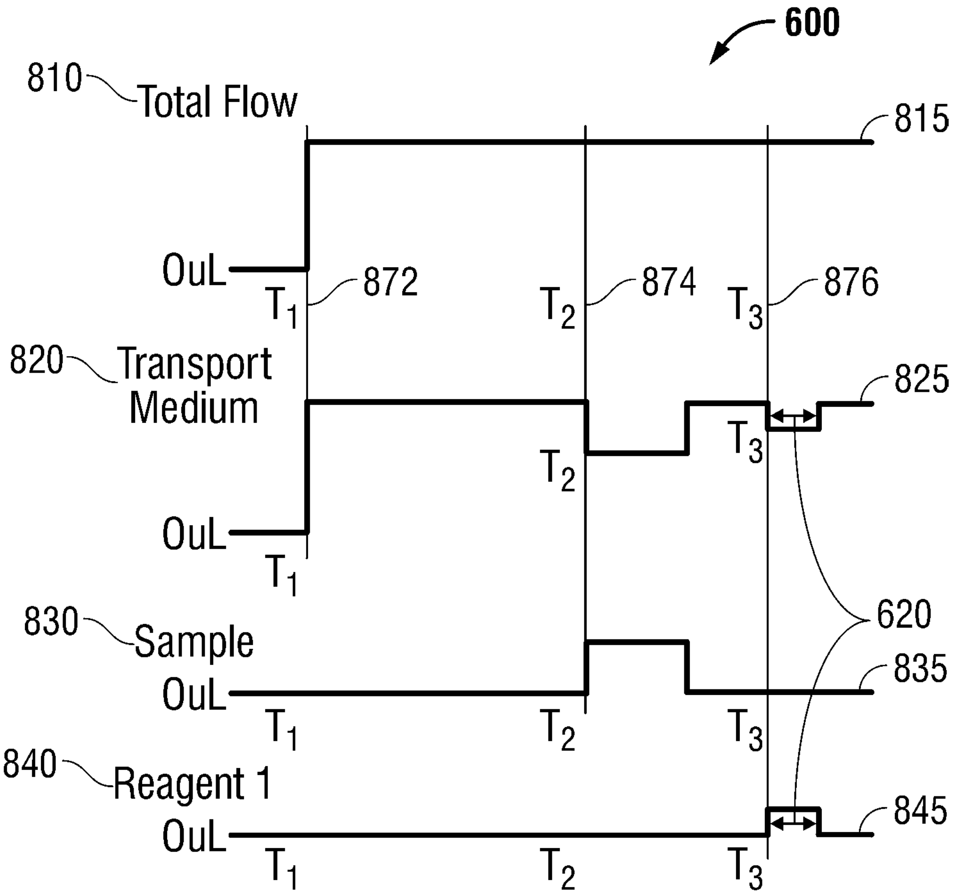
FIG. 6 illustrates exemplary flow rates in a system for regulating flow in a fluidic device with a single flow stream comprising a transport medium and a sample and one reagent.

FIG. 6 provides a timing diagram 600 that also shows flow rates at time $T_3$ 876 after injection of Reagent 1 (840). Depicted are flow rates 825 for transport medium 820, 815 for Total Flow 810, 835 for Sample 830, and 845 for Reagent 1 (840). With the sample in the stream, the first reagent injector, injector 1 (364) makes an addition of Reagent 1 (840) to the flow stream at $T_3$ 876 during a time interval 620. During the injection of the reagent 1 (840), FCC 310 adjusts the flow rate 825 of transport medium 820 to maintain Total Flow 815 at the target total flow rate 809. Timing this injection can be accomplished as a time function or through the use of a sensor (conductivity or other) can be placed in front of the injector to trigger the event. During the injection of sample 830, FCC 310 adjusts the flow rate 825 of transport medium 820 to maintain the Total Flow at the target total flow rate 809. In other words, $F_{TM}=F_{total}-F_{inj\ 2}$ during time interval 620.

Figure 7:
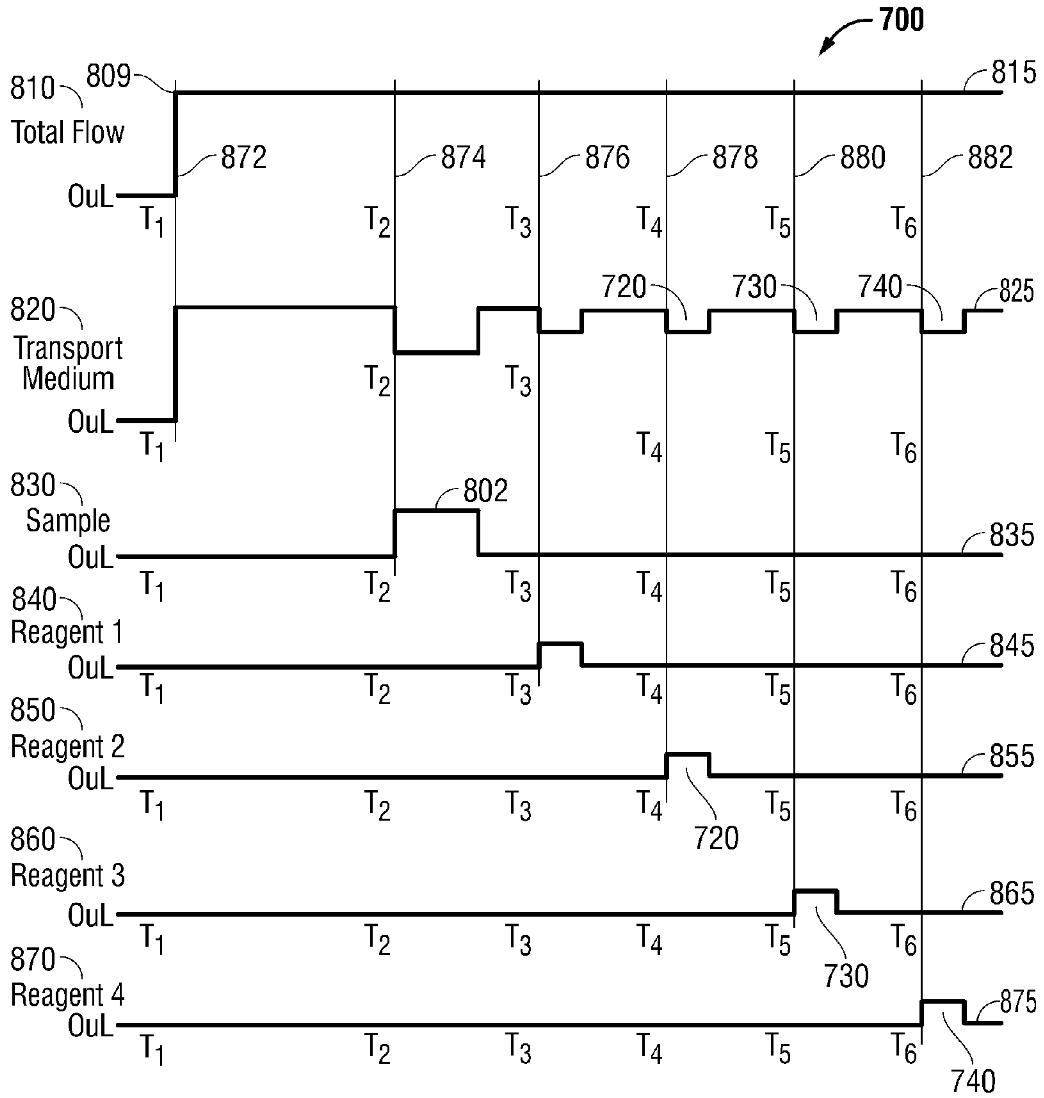
FIG. 7 illustrates exemplary flow rates in a system for regulating flow in a fluidic device with a single flow stream comprising a transport medium and a sample and four reagents.

FIG. 7 provides a timing diagram 700 that also shows flow rates at times $T_4$ 878, $T_5$ 880 and $T_4$ 882 after injection of Reagent 2 (850), Reagent 3 (860), and Reagent 5 (870), respectively. With a quantity 802 of sample 830 and reagent 1 (840) in the stream, the second reagent injector, injector 2 (370) makes an addition of Reagent 2 (850) to the flow stream at $T_4$ 878 during a time interval 720. At time $T_5$ 880, Reagent injector 3 (376) injects Reagent 3 860 into the stream during interval 730, and at time $T_6$ 882, Reagent injector 4 (382) injects Reagent 4 (870) into the stream during interval 740. During the injection of each reagent FCC 310 adjusts the flow rate of transport medium 820 to maintain the Total Flow 810 at the target total flow rate 809. During interval 720, while Reagent 2 (850) is being injected at flow rate $F_{inj\ 2}$, FFC 310 adjusts $F_{TM}$ so that it equals $F_{total}-F_{inj\ 2}$. Similarly, during interval 730, FFC 310 adjusts $F_{TM}$ so that it equals $F_{total}-F_{inj\ 3}$, and during interval 740, FFC 310 adjusts $F_{TM}$ so that it equals $F_{total}$−F(inj 4). Timing of these injections can again be accomplished as a time function or a sensor (conductivity or other) can be placed in front of the injector to trigger the event.

Figure 8:
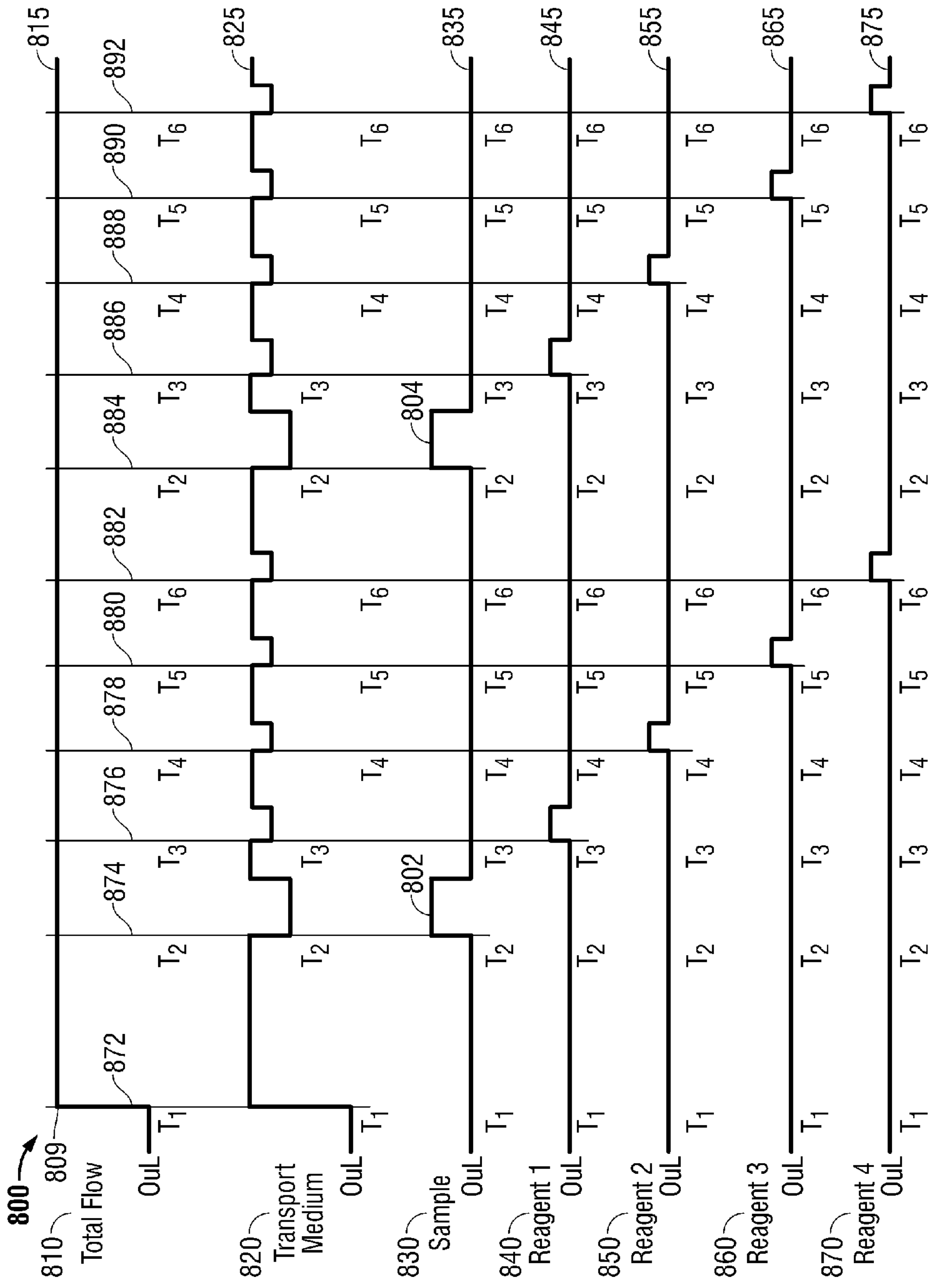
FIG. 8 illustrates an exemplary simple sequence of flow rates in a system for regulating flow in a fluidic device with a single flow stream comprising a transport medium and a sample and four reagents.

In a simple sequence a sample and all of its associated injections are completed prior to additional sample processing. When multiple samples are processed in a simple sequence, FFC 310 will make adjustments for each injection, preferably under the control of master controller 390, as illustrated in FIG. 8. FIG. 8 shows the serial processing of a first quantity 802 of sample 830, as also depicted in FIG. 7, and a second quantity 804 of sample 830, which is also processed by system 300 as depicted in FIG. 7. Second quantity 804 of sample 830 is injected into the flow stream at time $T_2$ 884, at which time FFC 310 reduces flow rate 825 of transport medium 820 by an amount equal to the flow rate 835 of sample 830 so that the total flow rate 815 remains constant at the target total flow rate 809. When a quantity of Reagent 1 (840) is injected at time $T_3$ 886 at flow rate 845, FFC 310 reduces flow rate 825 of transport medium 820 by an amount equal to the flow rate 845 of Reagent 1 (840) so that the total flow rate 815 remains constant at the target total flow rate 809. Similarly for quantities of Reagent 2 (850), Reagent 3 (860), and Reagent 4 (870) injected at times $T_4$ 888, $T_5$ 890 and $T_6$ 892, in each case FFC 310 reduces flow rate 825 of transport medium 820 by an amount equal to the flow rate of the injected reagent (855, 865, 875) to maintain the total flow rate 815 at the target total flow rate 809.

Figure 9:
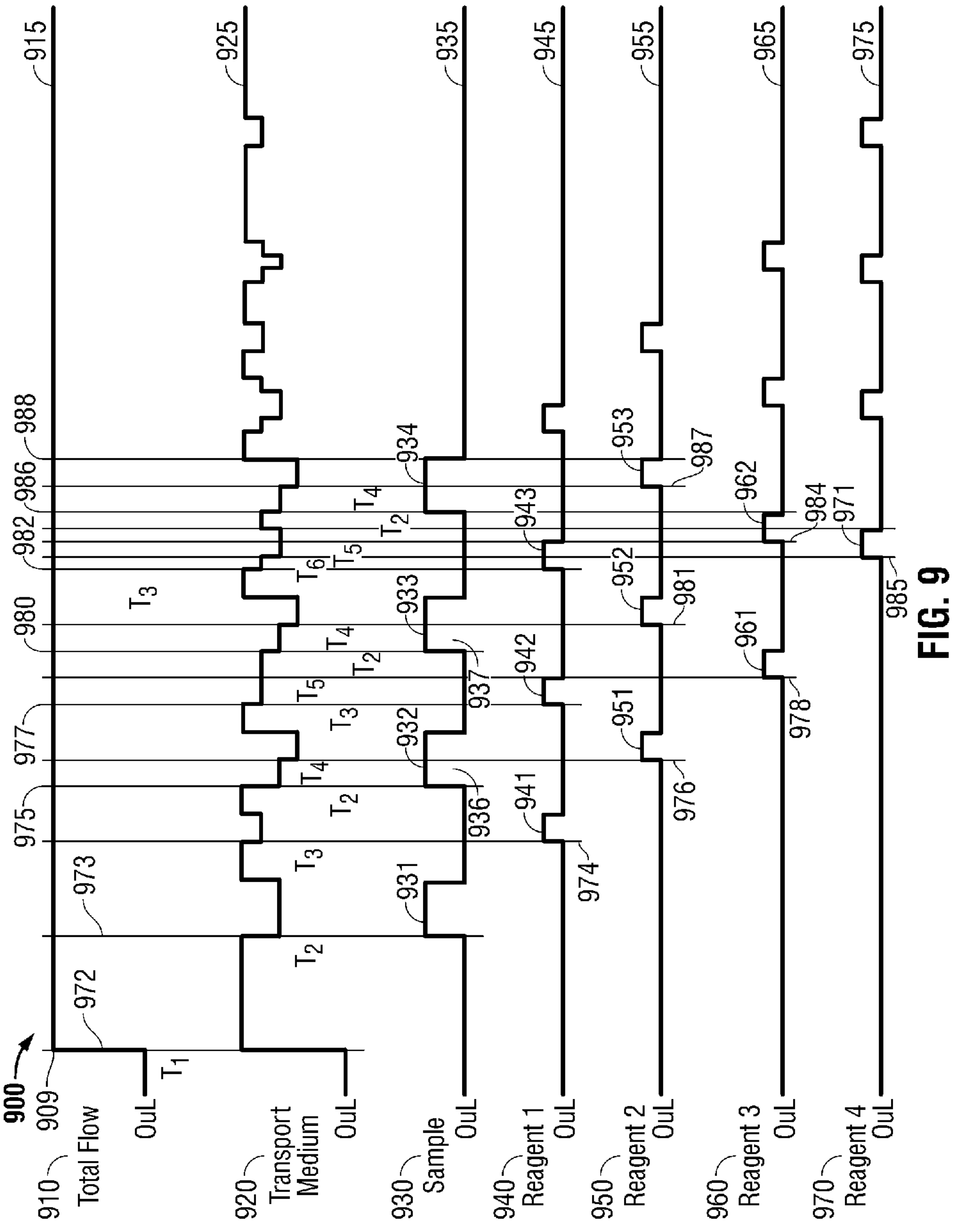
FIG. 9 illustrates exemplary flow rates during an oversampling sequence in a system for regulating flow in a fluidic device with a single flow stream comprising a transport medium and a sample and four reagents.

In an embodiment in which multiple samples are processed in an oversampling method (i.e., the first sample is still being processed when the second is injected), FCC 310 (preferably as controlled by master controller 390) will make adjustments for multiple injectors acting simultaneously as illustrated in FIG. 9. FIG. 9 provides a timing diagram 900 which depicts Total Flow rate 915 and flow rates 925 for transport medium 920, 935 for Sample 930, 945 for Reagent 1 (940), 955 for Reagent 2 (950), 965 for Reagent 3 (960) and 975 for Reagent 4 (970). When system 300 is initiated at time $T_1$ 972, FFC 310 brings flow rate 925 of transport medium 920 up to the target total flow rate 909. With no other flow sources, total flow 915 equals the flow rate 925 of transport medium 920. At time $T_2$ 973, a first quantity 931 of sample 930 is injected, and FFC 310 reduces $F_{TM}$ 925 by an amount equal to sample flow rate 935 during the interval while sample 931 is being injected to maintain $F_{total}$ 915 at the target total flow rate 909. At time $T_3$ 974, a first quantity 941 of Reagent 1 (940) is injected, and FFC 310 reduces $F_{TM}$ 925 by an amount equal to Reagent 1 flow rate 945 during the interval while the Reagent 1 (941) is being injected to maintain $F_{total}$ 915 at the target total flow rate 909.

Beginning with time $T_4$ 976, timing diagram 900 shows what happens when two or more samples or reagents are simultaneously added to the system. At time $T_2$ 975, a second quantity 932 of sample 930 is added during an interval 936, and FFC 310 reduces $F_{TM}$ 925 by an amount equal to sample flow rate 935 during interval 936 while the sample (932) is being added to maintain $F_{total}$ 915 at the target total flow rate 909. Beginning at time $T_4$ 976 during interval 936, a first quantity 951 of Reagent 2 (950). FFC 310 reduces $F_{TM}$ 925 by an amount equal to the sum of sample flow rate 935 and Reagent 2 flow rate 955 during the remainder of interval 936 to maintain $F_{total}$ 915 at the target total flow rate 909. At the end of interval 936, FFC brings sample flow rate 935 and Reagent 2 flow rate 955 back to 0 and transport medium flow rate 925 is restored to the target total flow rate 909.

At time $T_3$ 977, a second quantity 942 of Reagent 1 (940) is added, and FFC 310 reduces $F_{TM}$ 925 by an amount equal to Reagent 1 flow rate 945 to maintain $F_{total}$ 915 at the target total flow rate 909. At time $T_5$ 978, FFC 310 simultaneously stops adding Reagent 1 (940), i.e., brings Reagent 1 flow rate 945 to 0, and begins adding a first quantity 961 of Reagent 3 (960). FFC 310 reduces $F_{TM}$ 925 by an amount equal to Reagent 3 flow rate 965 to maintain $F_{total}$ 915 at the target total flow rate 909. In the example shown in FIG. 9, the flow rate 965 for Reagent 3 at time $T_5$ 978 is the same as Reagent 1 flow rate 945 at time $T_3$ 977, so there is no net change in the transport medium flow rate 925.

At time $T_2$ 980 in FIG. 9, a third quantity 933 of sample 930 is added during an interval 937, and FFC 310 reduces $F_{TM}$ 925 by an amount equal to sample flow rate 935 during interval 937 while the sample (933) is being added to maintain $F_{total}$ 915 at the target total flow rate 909. Beginning at time $T_4$ 981 during interval 936, a second quantity 952 of Reagent 2 (950) is added. FFC 310 reduces $F_{TM}$ 925 by an amount equal to the sum of sample flow rate 935 and Reagent 2 flow rate 955 during the remainder of interval 936 to maintain $F_{total}$ 915 at the target total flow rate 909. At the end of interval 936, FFC 310 brings sample flow rate 935 and Reagent 2 flow rate 955 back to 0 and transport medium flow rate 925 is restored to the target total flow rate 909.

At time $T_3$ 982, a third quantity 943 of sample Reagent 1 (940) is added, and FFC 310 reduces $F_{TM}$ 925 by an amount equal to Reagent 1 flow rate 945 to maintain $F_{total}$ 915 at the target total flow rate 909. Beginning at time $T_6$ 983, a first quantity 971 of Reagent 4 (970) is added, and FFC 310 further reduces $F_{TM}$ 925 by an amount equal to the sum of Reagent 1 flow rate 945 and Reagent 4 flow rate 975 to maintain $F_{total}$ 915 at the target total flow rate 909. At time $T_5$ 984, FFC 310 brings Reagent 1 flow rate 945 back to 0 and also begins adding Reagent 3 (960). Beginning at time $T_5$ 984, FFC 310 maintains $F_{TM}$ 925 at a flow rate equal to $F_{target}$ 909 minus the sum of Reagent 3 flow rate 965 and Reagent 4 flow rate 975, thereby maintaining $F_{total}$ 915 at the target total flow rate 909. At time 985, FFC 310 brings Reagent 4 flow rate 975 back to 0 and increases $F_{TM}$ 925 so that it equals $F_{target}$ 909 minus Reagent 3 flow rate 965, and FFC 310 maintains this flow rate until time $T_2$ 986 when it brings Reagent 3 flow rate 965 back to 0. Also at time $T_2$ 986, FFC 310 adds a fourth quantity 934 of sample 930 to the stream. At time $T_2$ 986, FFC 310 increases transport medium flow rate 925, to compensate for Reagent 3 flow rate 965 going to 0, and decreases transport medium flow rate 925, to compensate for the increase in sample flow rate 935, with the net effect being that FFC 310 reduces $F_{TM}$ 925 so that it equals $F_{target}$ 909 minus sample flow rate 935. This flow rate is maintained time $T_4$ 987, when FFC 310 begins adding a third quantity 953 of Reagent 2 (950) and decreases $F_{TM}$ by the amount of Reagent 2 flow rate 955, so that $F_{TM}$ equals target total flow rate 909 minus the sum of sample flow rate 935 and Reagent 2 flow rate 955. At time 988 FFC 310 takes sample flow rate 935 and Reagent 2 flow rate 955 to 0 and restores transport medium flow rate 925 to the target total flow rate 909.

Figure 10:
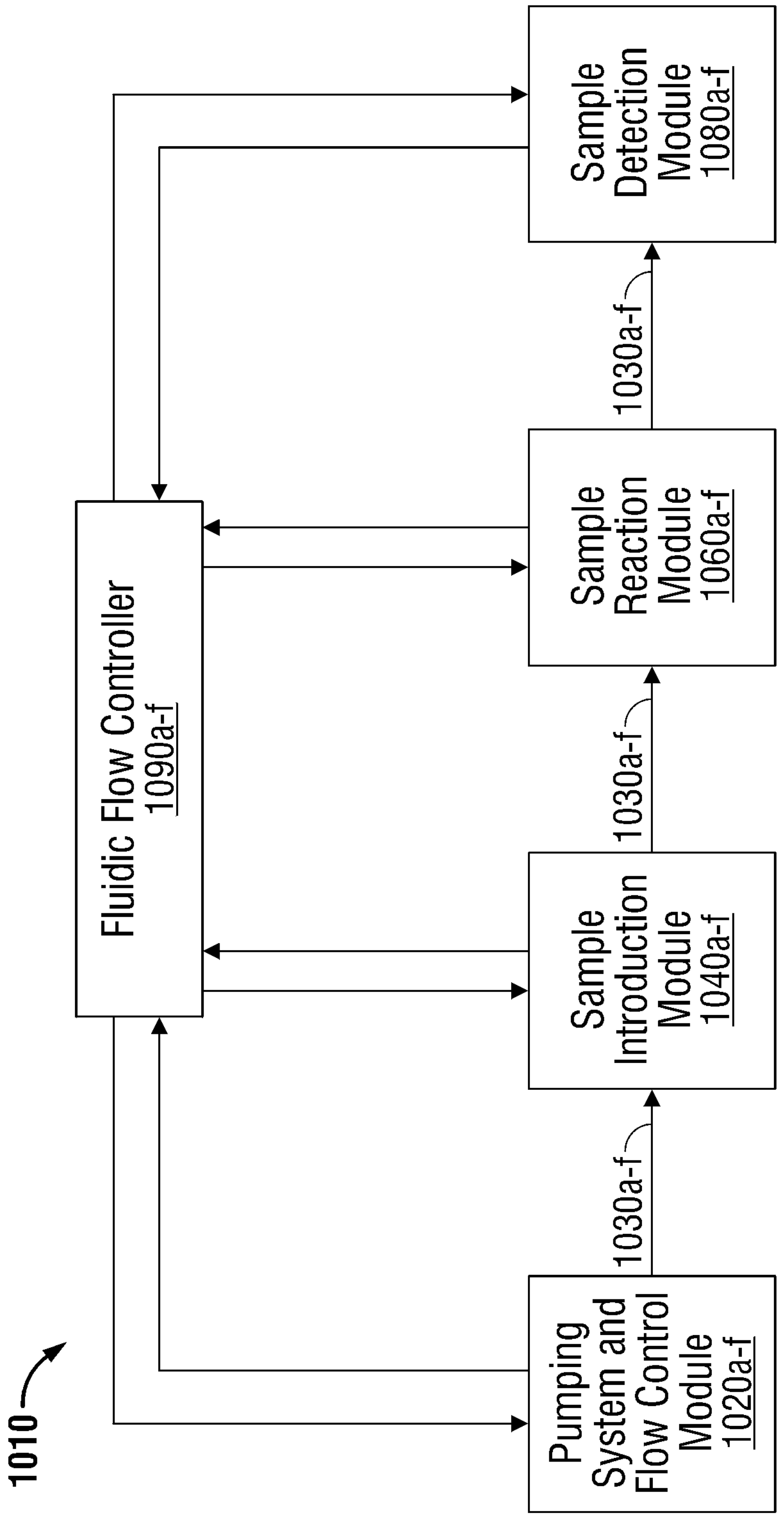
FIG. 10 illustrates an exemplary embodiment of a system for regulating flow in a fluidic device comprising a pumping system and flow control module, a sample introduction module, a sample reaction module, and a sample detection module.
Figure 12:
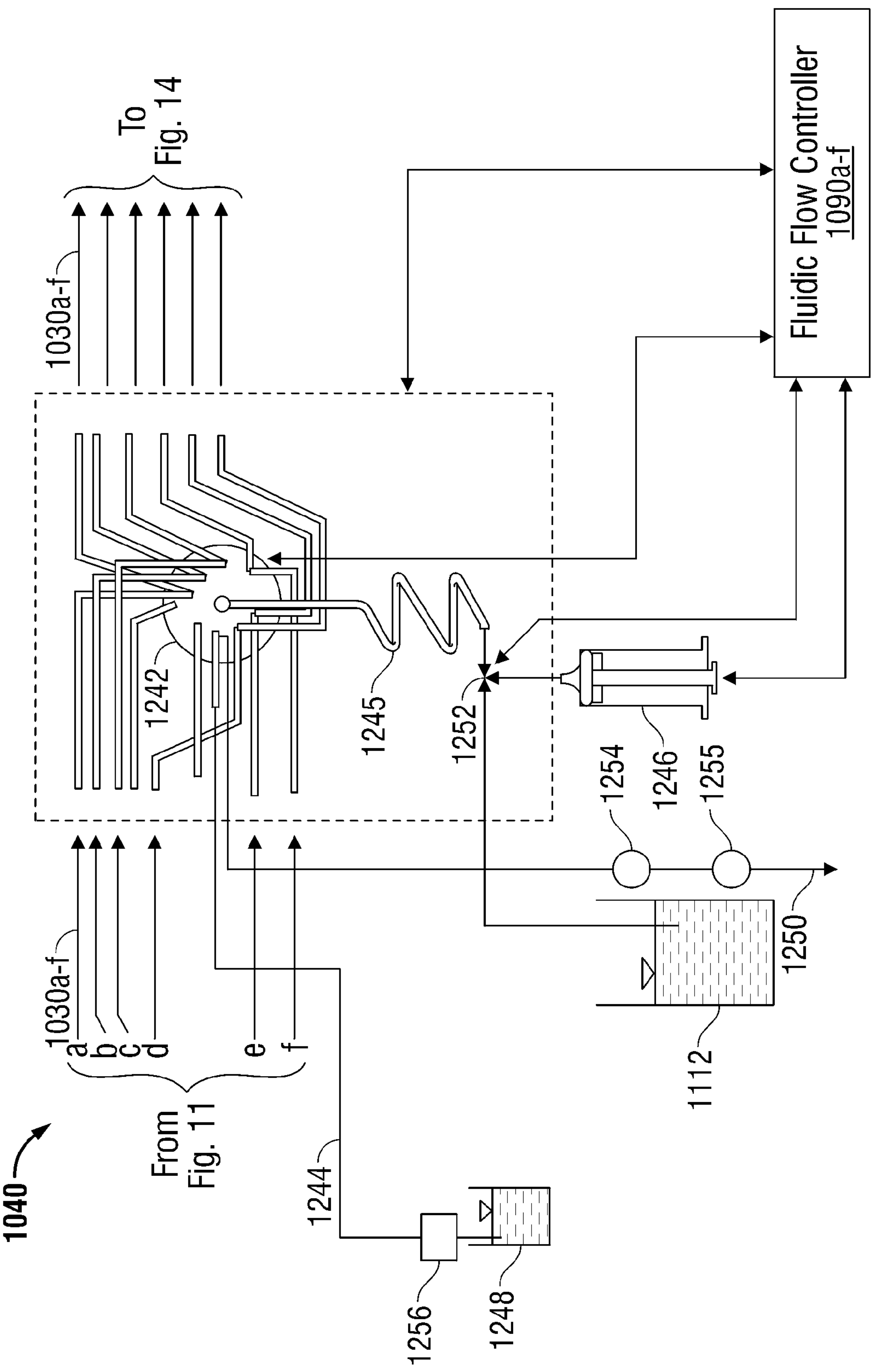
FIG. 12 illustrates an exemplary embodiment of a sample introduction module in a system for regulating flow in a fluidic device.
Figure 13:
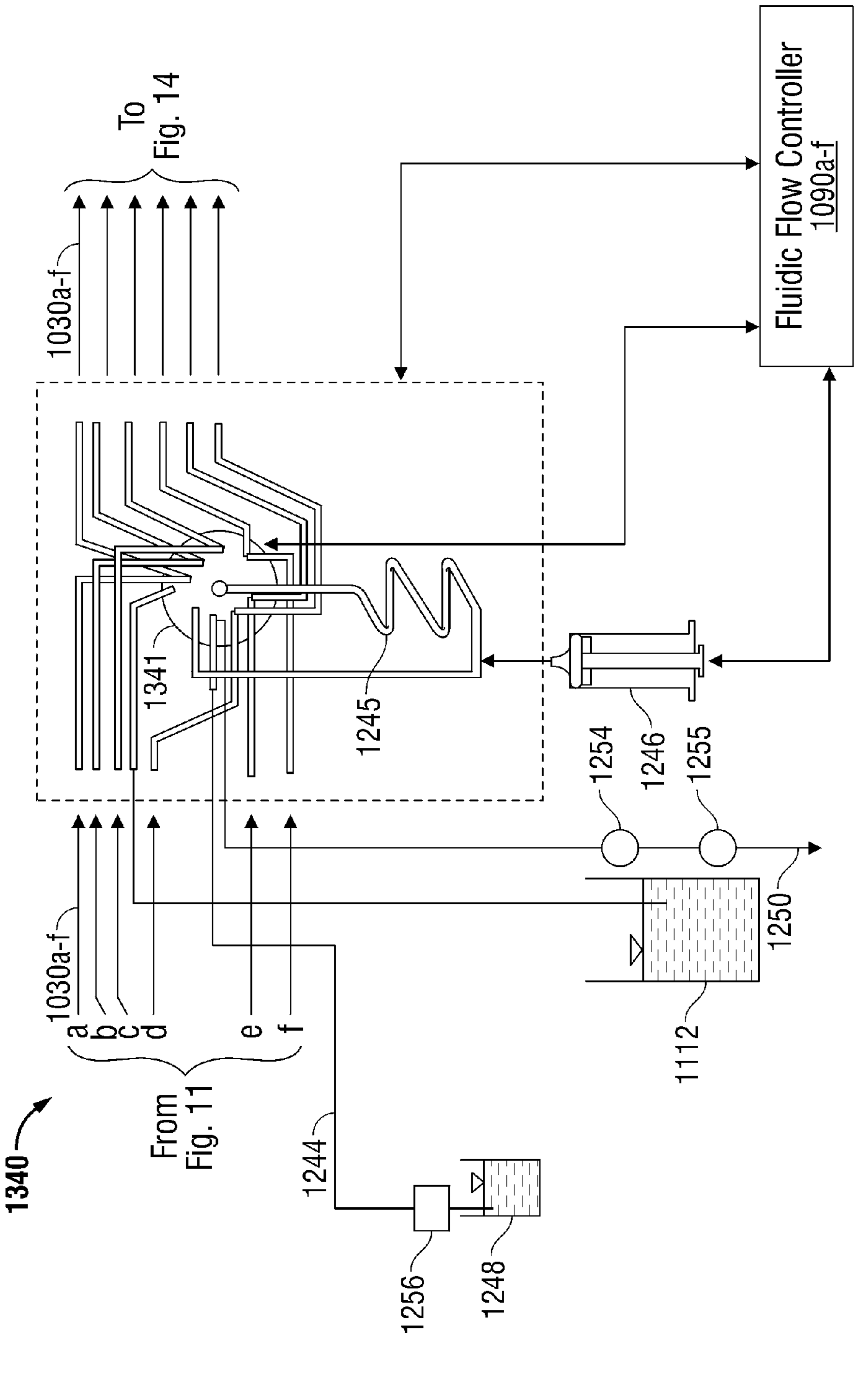
FIG. 13 illustrates an alternative embodiment of a sample introduction module in a system for regulating flow in a fluidic device.
Figure 14:
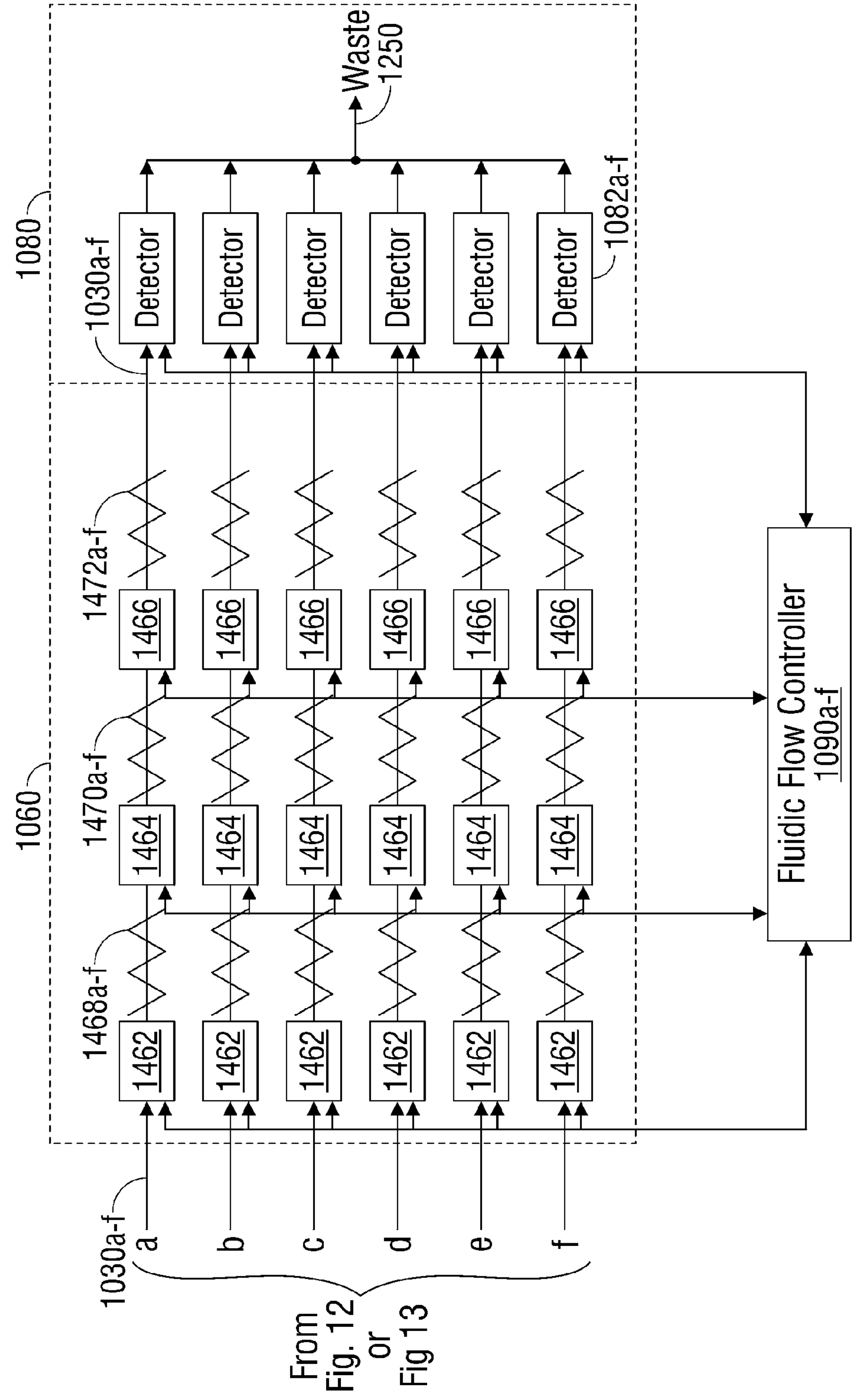
FIG. 14 illustrates a exemplary implementation of a sample reaction module and a sample detection module in a system for regulating flow in a fluidic device.

FIGS. 10 through 14 illustrate an embodiment of a system and method of regulating the flow of a fluidic device comprising one or more channels of analysis. System 1010 as depicted in FIG. 10 comprises four modules: a pumping system and flow control module 1020, a sample introduction module 1040, a sample reaction module 1060, and a sample detection module 1080. The pumping system and flow control module 1020 employs a fluidic pump 1114 (shown in FIG. 11) that imparts the motive force to a transport medium flowing via the analytical streams 101030*a-f* of the system 1010. One or more programmable fluidic flow controllers 1090*a-f* are employed in conjunction with the system 1010 to control the flow of the transport medium within each of the analytical streams 1030*a-f*. The fluidic flow controllers 1090*a-f* control the flow rate of the transport medium through the analytical streams 1030*a-f* in order to maintain a constant flow at the detectors 1082*a-f* (FIG. 15) within the sample detection module 1080 even while samples are injected into the analytical streams 1030*a-f* within the sample introduction module 1040 (FIG. 12) and reagents are injected into the analytical streams 1030*a-f* within the sample reaction module 1060. A constant flow at the detectors 1082*a-f* (FIG. 14) does not necessarily imply that a constant flow is maintained at all points along the analytical streams 1030*a-f*. Typically, the flow rate of the analytical streams 1030*a-f* is not constant, but is controlled to properly sequence the addition of the sample and one or more reaction reagents and to permit one or more reaction processes prior to analysis by the detectors 1082*a-f* (FIG. 14).

The system 1010 preferably is not a series of independent modules 1020, 1040, 1060, 1080, but rather is a system comprised of elements that permit improved quantification, throughput (samples per unit time), up time (lower downtime required for maintenance, re-alignment, and calibration), greater flexibility in set up, lower reagent use, limited generation of waste and greater reliability. This system 1010 is described and illustrated in modular form only for the ease of disclosure. While subsystems could be made in a modular form, the system 1010 of a preferred implementation has elements that, while performing varying functions, are closely interdependent and holistically controlled by one or more programmable fluidic flow controllers 1090*a-f*.

Figure 11:
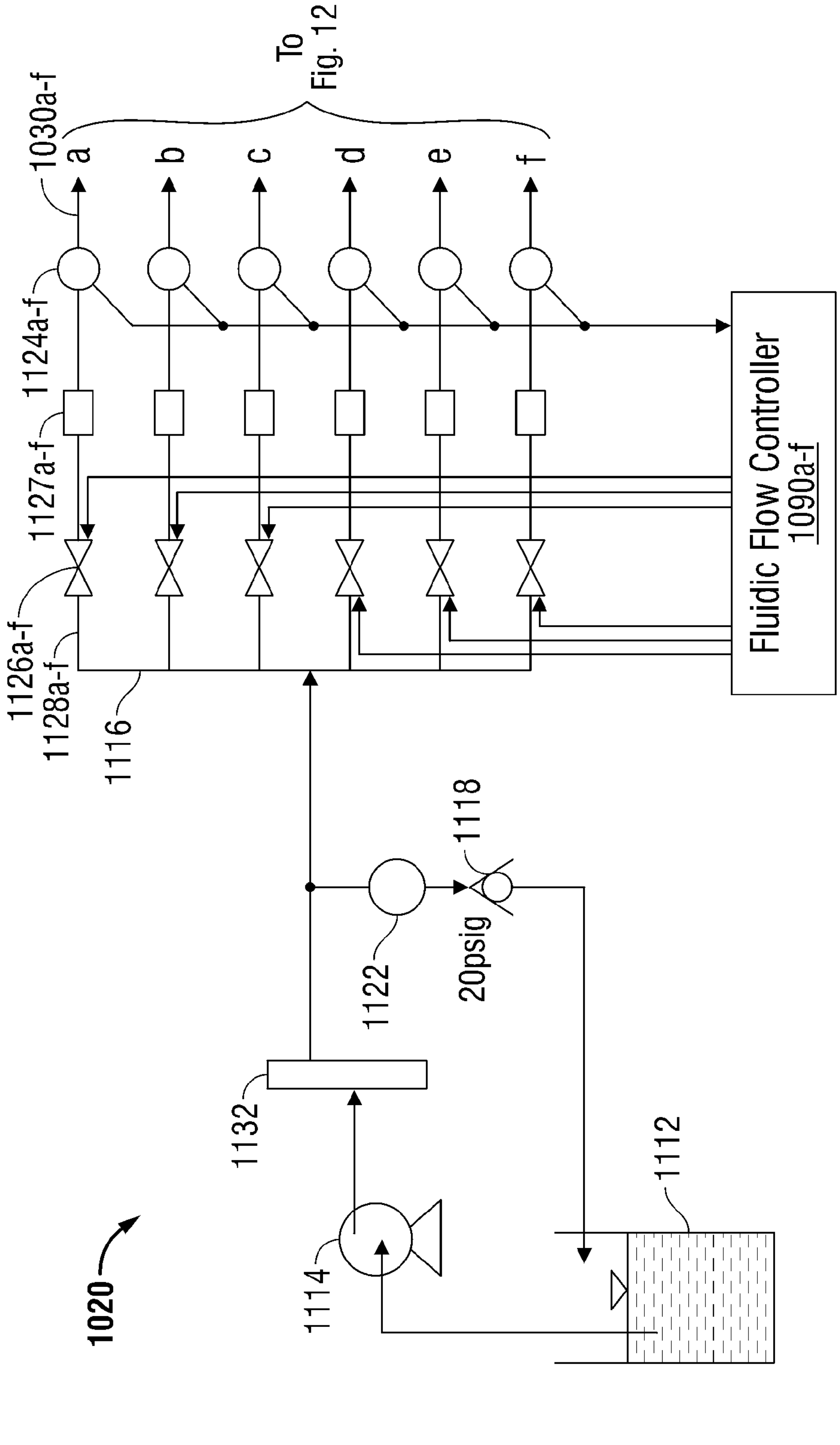
FIG. 11 illustrates an exemplary implementation of a flow control module in a system for regulating flow in a fluidic device.

As illustrated in FIG. 11, the pumping system and flow control module 1020 preferably comprises a fluidic pump 1114, a filter element 1132, a manifold 1116, a pressure sensor 1122, a back pressure regulator 1118, and a reservoir 1112, The nature and operation of fluidic pump 1114, filter element 1132, pressure sensor 1122, back pressure regulator 1128 and reservoir 1112 of transport medium are described in more detail above as, respectively, pump 327, filter 329, sensor 321, back pressure regulator 323 and reservoir 325 of transport medium 326 of constant pressure system 320 of exemplary system 300 illustrated in FIG. 3. The fluidic pump 1114 draws a transport medium from reservoir 1112 and directs it to the one or more transport streams 1030*a-f* through manifold 1116. Fluidic pump 14 preferably maintains a constant flow rate across a filter element 1132 that is positioned between the pump 1114 and the manifold 1116.

As shown in FIG. 11, the back pressure regulator 1118 is disposed in a side stream positioned downstream of the fluidic pump 1114 between the filter element 1132 and the manifold 1116. The back pressure regulator 1118 maintains the flow of the transport medium from the fluidic pump 1114 at a constant pressure. Preferably, the back pressure regulator 1118 maintains the pressure at 20 psig such that the pressure to the manifold 1116 and each of the analytical streams 1030*a-f* is also maintained at 20 psig. The arrangement of the pumping system and flow control module 1020, as shown in FIG. 11, provides a restrictive control on the pressure and flow of the transport medium to the manifold 1116. The back pressure regulator 1118 operates by permitting the flow of transport medium therethrough at a varying flow rate to maintain the back pressure at a desired level. Any transport medium flowing through the back pressure regulator 1118 is returned to the fluid reservoir 1112 supplying transport medium to the pumping system and flow control module 1020. The flow of transport medium across the back pressure regulator 1118 will be orders of magnitude higher than the total flow to and through the individual analytical streams 1030*a-f*. Therefore, the flow of transport medium to the analytical streams 1030*a-f* via manifold 1116 will have little to no effect on the pressure maintained by the flow of transport medium through the back pressure regulator 1118. The output signal from pressure sensor 1122, positioned between the filter element 1132 and the back pressure regulator 1118, is used to control the flow rate of the fluidic pump 1114 either manually or through automatic feedback control. However, the primary purpose of pressure sensor 1122 is to determine the supply side pressure. As is well known in the art, the differential pressure between the supply side pressure and the individual analytical stream pressures may be used to determine the individual analytical stream flows.

As further illustrated in FIG. 11, manifold 1116 employs six flow elements 1128*a-f* (in an embodiment, capillary tubings) with differential pressure sensing that are used to transport the analytical streams 1030*a-f* comprising the sample/analyte, transport medium, and reagents. Additional flow elements (not shown) may be coupled to the manifold 1116 for the analysis of additional analytical streams (not shown). Likewise, fewer than six flow elements (not shown) may be coupled to the manifold 1116 for the analysis of fewer analytical streams (not shown). In a preferred implementation, each of the flow elements 1128*a-f* are sized for a desired flow rate. A variable sized orifice (VSO) valve assembly 1126*a-f* is also preferably disposed within each of the flow elements 1128*a-f* to further control the absolute flow of transport medium through the flow elements 1128*a-f* (i.e., the analytical streams 1030*a-f*). VSO valve 1126*a-f* can comprise a voltage-controlled orifice. Each analytical stream 1030*a-f* has a programmable fluidic flow controller 1090*a-f*, which controls the flow rate of transport medium through flow elements 1128*a-f* as well as the time and spatial addition of sample and reagents to the analytical streams 1030*a-f*.

Within pumping system and flow control module 1020, the fluidic flow controllers 1090*a-f* are employed to regulate the flow transport medium through the flow elements 1128*a-f* of each analytical stream 1030*a-f* by controlling the VSO valve 1126*a-f* of each flow element 1128*a-f* such that a constant flow is delivered to detectors 1082*a-f* (FIG. 14). The fluidic flow controllers 1090*a-f* regulate the size of the orifice in the VSO valves 1126*a-f* based upon flow rate feedback data received from flow sensing elements 1124*a-f* (e.g., pressure sensors/meters, flow sensors/meters, or any other sensing element) disposed within each of the flow elements 1128*a-f* downstream of the VSO valves 1126*a-f*. Alternatively, a capillary restriction 1127*a-f* may be positioned within each of the flow elements 1128*a-f* and sized to control the flow of each of the analytical streams 1030*a-f*. The capillary restrictions 1127*a-f* may be used either alone or in conjunction with the VSO valves 1126*a-f*. Because the pumping system and flow control module 1020 preferably utilizes a constant pressure pump 1114, a shut down of the pump 1114 is required to fully shut down the module 1020. Therefore, fluidic flow controllers 1090*a-f* must also prevent the back flow of sample and/or reagents from the sample reaction module 1060 when transport medium is not being pumped by pump 1114. Back flow of sample and/or reagents is most likely to occur either during sample introduction or addition of reagents into the analytical streams 1030*a-f*. Back flow of sample and/or reagents into the transport medium reservoir 1112 may be prevented by using fluidic flow controllers 1090*a-f* to fully close the VSO valves 1126*a-f*.

As illustrated in FIG. 12, the sample introduction module 1040 preferably comprises a syringe pump 1246, a three-way valve 1252, an isolation loop 1245, a sample prime pump 1255 and one or more multi-port valves 1242. The purpose of the sample introduction module 1040 is to acquire a sample, inject a programmed amount of the sample into one or more analytical streams 1030*a-f* at the appropriate time and at the appropriate delivery rate, and to purge/rinse the isolation loop 1245 in preparation for the next sample injection. The syringe pump 1246 draws a sample from a sample source 1248 through the sample line 1244, the multi-port valve 1242, and into the isolation loop 1245. The isolation loop 1245 prevents the entry of the sample into the cavity of the syringe pump 1246, thereby preventing the transference of one sample into another (i.e., carrier-over). The fluidic flow controller 1090*a-f* associated with each analytical stream 1030*a-f* controls the operation of the syringe pump 1246, the three-way valve 1252 and the rotary multi-port valve 1242 to inject the aspirated sample into the proper analytical stream 1030*a-f* at the appropriate time and delivery rate. The syringe pump 1246 may also draw transport medium from reservoir 1112 through the three-way valve 1252 for delivery to each analytical stream 1030*a-f* via the isolation loop 1245 and the multi-port valve 1242. As the analytical streams 1030*a-f* are each selected for sample injection and analysis, the fluidic flow controller 1090*a-f* associated with the selected analytical stream 1030*a-f* also controls its VSO valve 1126*a-f* to increase or decrease the flow of transport medium through the selected flow element 1128*a-f* (i.e., analytical stream 1030*a-f*) (FIG. 11) such that, with the injection of the sample, a constant flow and/or pressure is achieved at the detector 1082*a-f* (FIG. 5). However, the pressure at which the sample is introduced into the analytical streams 1030*a-f* preferably remains constant during the injection process in order to facilitate the fluidic flow controllers 1090*a-f* in maintaining a constant flow of the analytical streams 1030*a-f* at the detectors 1082*a-f* (FIG. 14). The fluidic flow controllers 1090*a-f* use one or more microcontrollers and/or microprocessors to synchronize in time and/or volumetric space the introduction of sample into the analytical streams/channels 1030*a-f*. Exemplary fluidic flow controllers 1090*a-f* include controller 420 of FFC 310 and master controller 390 of system 300, as illustrated in, and described in connection with, FIGS. 3-4. In an embodiment, fluidic flow controllers 1090*a-f* are all integrated in a single controller; in an alternative embodiment, each analytical stream 1030*a-f* has a dedicated fluid flow controller 1090*a-f*.

As further shown in FIG. 12, the arrangement of the sample introduction module 1040 permits the isolation loop 1245 to be flushed or rinsed between samples. When the syringe pump 1246 is filled with the transport medium from reservoir 1112, the isolation loop 1245 is flushed by the transport medium flow from the syringe pump 1246 when the multi-port valve 1242 is selected to direct the transport medium flow to the waste disposal line 1250. By appropriately cycling the three way valve 1252, the syringe pump 1246, and the position of the multi-port valve 1242, sample or transport medium can be pulled from the sample source 1248 or the reservoir 1112, respectively, and either introduced into a specific analytical stream 1030*a-f* or sent to the waste disposal line 1250. Additionally, one or more sensors 1254 may be positioned within the waste disposal line 1250 to sense the presence (or lack thereof) of fluid therein, and thus minimize the wasteful consumption of sample due to the overloading of the waste disposal line 1250. In a preferred implementation of the invention, sensor 1254 is a conductivity sensor, however, other types of sensors may be used including, but not limited to, optical sensors, capacitance sensors, or pressure sensors. An autosampler probe 1256, well known to those of skill in the art, may be employed in conjunction with the sample line 1244 of the sample introduction module 1040 to automate and speed up, the analysis of multiple samples.

In another embodiment of the system, as shown in FIG. 13, an eight-way valve 1341 is used in place of the multi-port valve 42 of FIG. 3. The eight-way valve 1341 incorporates the three-way valve 1252 of FIG. 12. The arrangement and operation of the sample introduction module 1340 is otherwise the same as shown and described with respect to the sample introduction module 1040 shown in FIG. 12. An embodiment of an eight-way valve 1341 is discussed below.

In an embodiment, sample prime pump 1255 is preferably positioned within the waste disposal line 1250 to prime the sample line 1244 with sample from sample source 1248 so that no air or fluid contamination is aspirated into the isolation loop 1245 via the valve (1242 or 1341) during operation of the syringe pump 45 to draw sample.

While it is preferable that the introduction of sample into the analytical streams 1030*a-f* directs the flow of the analytical streams 1030*a-f* toward the sample reaction module 1060 and detection module 1080, the flow within the analytical stream/channel 1030*a-f* need not be single directional. For example, during sample injection, the flow within the analytical stream 1030*a-f* may briefly reverse to allow rapid injection of the sample into the analytical stream 1030*a-f*. However, the sample injection cannot overfill the volume of the flow element 1128*a-f* and flow back to the pumping system module 1020, which could result in some of the sample being transferred into the transport medium reservoir 1112 via backflow pressure regulator 1118. Nevertheless, the back-fill capability (i.e., limited reverse flow) permits rapid filling of the individual analytical stream or channel 1030*a-f*, and thereby permits the sample introduction module 1040 to rapidly service multiple analytical channels 1030*a-f* so as to achieve a high analytical throughput.

For non-segmented flow, stipulating both a constant flow rate and flow in a single downstream direction requires the fluidic flow controller 1090*a-f* to introduce the sample via syringe pump 1246 at the proper time and flow rate so as to not "push" sample upstream within the analytical streams/channels 1030*a-f*, yet quantitatively transfer the sample to a known volume of transport medium (i.e., a known dilution of sample/analyte, ranging from no dilution to a system or operator determined value). The flow of the analytical streams 1030*a-f* need not be truly non-segmented and may alternatively consist of spatial regions of higher and lower concentrations of sample/analyte (i.e., known stepwise levels or continuous gradients of sample/analyte). In contrast, segmented flow may be achieved by injecting the typically aqueous sample into the transport medium within the analytical stream 1030*a-f*, thereby creating a pocket or bolus of analyte sandwiched between the upstream and downstream transport medium. As previously described, the transport medium could be highly purified water (i.e., de-ionized water), a gas (e.g., air, nitrogen, helium, etc.), a hydrophobic media, such as perfluorinated polyether (PFPE), multiply-alkylated cyclopentanes, or any other highly hydrophobic fluid, or any other substance that can create a phase boundary between the analytical sample and the transport medium. Alternatively, segmented flow can be created through the classical method of injecting slugs of air into the transport medium of the analytical streams 1030*a-f* prior to the point of sample injection within the sample introduction module 1060.

As illustrated in FIG. 14, the sample reaction module 1060 of each analytical stream 1030*a-f* preferably comprises one or more reagent inlets 1462*a-f*, 1464*a-f*, 1466*a-f*, and one or more mixing loops/volumes 1468, 1470, 1472. In the sample reaction module 1060, reagents are injected at the proper time, place, and flow rate through inlets 1462*a-f*, 1464*a-f*, 1466*a-f* positioned along the length of the analytical streams 1030*a-f* in order to provide constant flow to the detectors 1082*a-f* of the sample detection module 1080, which is also illustrated in FIG. 14. The fluidic flow controllers 1090*a-f* adjust the transport medium flow inversely in relation to the added flow of the sample in the sample introduction module 1040 and the reagents in the sample reaction module 1060. One or more reaction sequences may be performed on each of analytical streams 1030*a-f* to convert the sample into a reaction product (i.e., analyte) that permits quantification and characterization by the detectors 1082a-f, Thus, the sample reaction module 1060 preferably has multiple mixing loops/volumes 1468a-f, 1470a-f, 1472a-f to permit multiple reaction sequences. As illustrated in connection with system 300, the user can use and substitute different configurations of mixing loops/volumes 1468a-f, 1470a-f, 1472a-f. One or more reaction chemistries/processes may also be performed on each of the analytical streams 1030a-f, For example, electrochemical cells, ion exchange, oxidation or reduction chemistries, ultraviolet sources, heat sources, active metal surfaces, catalytic materials, phase separation elements, and digestions may be employed to produce the desired reaction product for quantification and characterization by the detectors 1082a-f. Furthermore, each analytical stream 1030a-f may be configured to have one or more samples present at any given time in a serial arrangement (not shown) along the length of the analytical stream 1030a-f. After each analytical stream 1030a-f has been analyzed at the detectors 1082a-f of sample detection module 1080, the analytical streams 1030a-f are sent to the waste disposal line 1250. Alternatively, one or more of the analytical streams 1030a-f can be recycled to the same or a different channel for further reaction processes (path switching).

As generally shown in FIG. 10, an embodiment of the system and method of the invention permits a more accurate quantification and/or characterization of the analytes of interest to be achieved. As previously disclosed, the use of a syringe pump 1246 (FIGS. 12 and 13) in conjunction with the fluidic flow controllers 1090a-f permits control of not only the volume of the sample injection into each analytical stream 1030a-f but also the precise timing of when the sample injection begins and the time period over which the sample injection occurs. When dynamically coupled with the pumping system and flow control module 1020 (FIG. 11) and the sample reaction module 1060 (FIG. 14), rapid sample injection techniques become possible along with the controlled dilution of the sample and the use of either segmented flow or non-segmented flow.

Additional techniques, such as auto dilution of sequential analyses, testing for reaction completion by adding excess reagents, determination of kinetic rate information (e.g., reaction/residence time in reactor as function of flow rate versus reaction response), and auto-optimization for method development, may each be employed individually or collectively with one or more implementations of the invention. For example, auto dilution of sequential analyses can occur by either increasing the flow rate of the transport medium or by injecting/introducing less sample into the transport medium of the analytical streams by employing a smaller sample volume. Furthermore, as previously disclosed, path switching may be employed to improve throughput by allowing a first portion of an analytical stream to proceed along a first reaction pathway (i.e., to be subjected to a specific set of reagents and reaction processes), and a second portion of the analytical stream (or its reaction product) to be routed into a parallel second reaction pathway and subjected to alternative reagents and reaction processes. Several analytical determinations may then be conducted using one or more detectors including, but not limited to, detection of analytes in the first and/or second portions of the analytical stream, followed by detection of analytes in the first reaction product, and finally, detection of analytes in the second reaction product.

A conventional embodiment of an 8-port rotary valve comprises eight radially-arranged input/output ports (labeled A thorough H) and a center port (S or Common) and is configured in a way that allows it to be connected to any one of the eight ports independently. The valve is typically connected to an electrical actuator, for example a stepper motor, which is capable of turning the rotor plate, and through control electronics this actuator is commanded to rotate to the desired port. A motive force provider, for example a syringe pump, typically is connected to the center port, and the syringe pump can aspirate or expel through whatever input/output port is connected to the center port by the actuator.

A conventional 8-port valve can be adapted for use in a method and system for regulating flow in a fluidic device and, in particular, for use as valve 1341 in the embodiment shown FIG. 13, Such an embodiment preferably includes two primary differences from a conventional embodiment of an 8-port valve. First, one port, "H" is relocated to a second connection pattern on a different outer radius from ports A-G, and an additional port ("DI") is disposed on the same outer radius as port H and connected to a source of a transport medium such as DI Water. These ports (H and DI) can only be connected when the valve is rotated to the "H" position, and in any other position both port "H" and the DI port are blocked. When the valve is rotated to the "H" port the common is blocked off and aspirating the syringe pump will draw DI water to the front of the syringe bypassing the Isolation loop. Second, the other seven ports are modified to have a "Tee" built in. Each of the other ports (the "flow through ports") has an input conduit and an output conduit. Port C, for example, will have an input conduit $C_{in}$ and an output conduit $C_{out}$. When the rotary valve points to any position away from port C (i.e., A-B, D-H), there is no path to the common port and transport medium flows through $C_{in}$ and out $C_{out}$ with no change or addition. When the rotary valve points to port C, however, there is an open "Tee" between the center port and $C_{in}$ and $C_{out}$, so that when the syringe pump dispenses sample into the center port, the transport medium from $C_{in}$ and the sample from the syringe pump both flow out through $C_{out}$. This embodiment of a modified valve can support six channels of analysis.

Figure 15A:
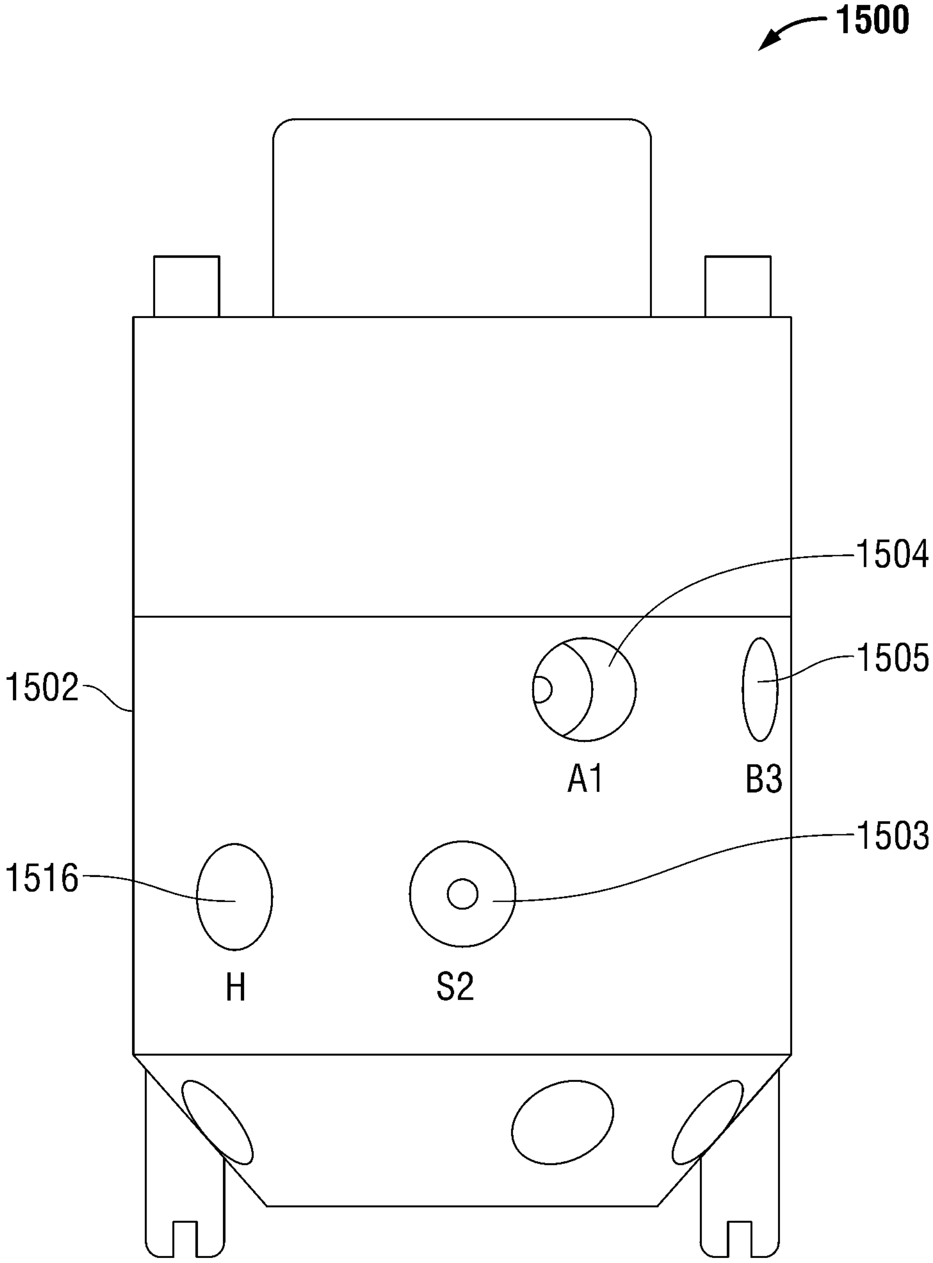
FIGS. 15A-E depict an exemplary embodiment of a valve adapted for use in a method and system for regulating flow in a fluidic device.

FIGS. 15A-E illustrate valve 1500, an exemplary embodiment of the modified valve described above. Although the exemplary embodiment shown FIGS. 15A-E supports only three different channels of analysis, those of ordinary skill in the art will appreciate that the structure disclosed herein can be adapted to support six channels of analysis and to serve the function of valve 1341 in FIG. 13. FIG. 15A illustrates a side view of valve 1500 showing valve body 1502, input conduit portals A1 (1504) and B1 (1505) and conduit portals H (1516) and S2 (1503).

Figure 15B:
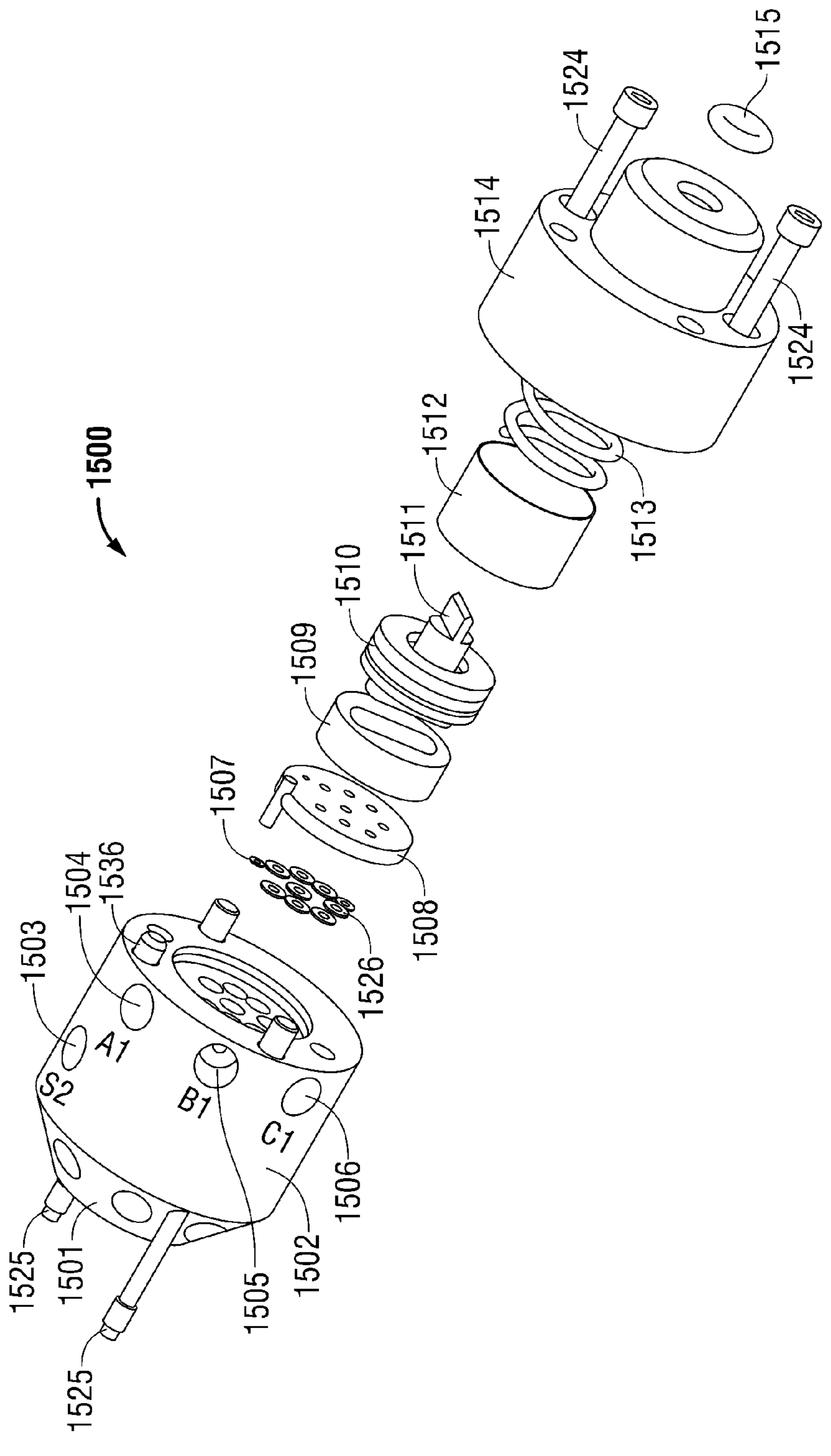

FIG. 15B is an exploded view of the components of valve 1500 including valve top 1501, and valve body 1502 comprising conduit portals S2 (1503), A1 (1504), B1 (1505), and C1 (1506). Stator 1508 is fixed in place with dowel pin means 1536 and 1507 and is drilled with, preferably, ten penetrations needed to interface with rotor 1509. The penetrations are organized as a center port with two hole patterns at different radii from the center. The inner radius has seven penetrations every 22.5° starting with the penetration corresponding to the A port. The outer radius has penetrations for the H port and the DI port, The penetrations correspond to conduits between center port S1 (the center port) (1520), sweep sweep ports A-C, and standard ports D-F (on the inner circle). There is no penetration on the inner circle for the H port (1516). When the H port (1516) is selected there is no flow through the center port; however, the outer circle connects the H port (1516) to a source of transport medium such as DI (not shown) through the DI port. Seal washers 1426 prevent leakage as fluid flows through the penetrations. Stator 1508 is coupled to rotor 1509 which embraces thrust bearing 1510. Valve blade 1511 is disposed within thrust bearing 1510 and sleeve washer 1512, which surrounds spring 1513 supported by valve cap 1514. The entire assembly is joined together by screws 1524, screw bodies 1525, and screw knurls (unnumbered). When mounted to an actuator chassis (not shown) the valve blade 1511 interfaces with the actuator (not shown) to provide positioning of the valve.

Figure 15C:
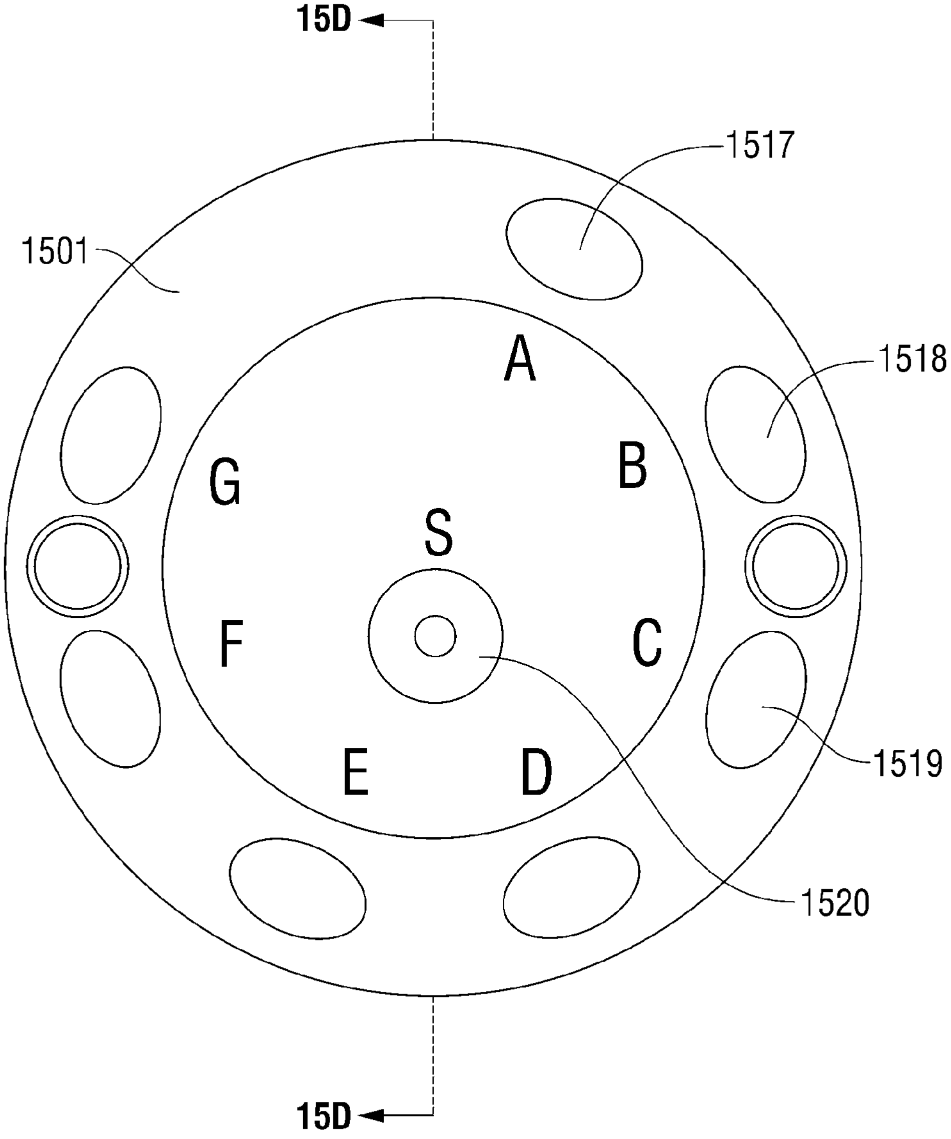

FIG. 15C illustrates valve top 1501 comprising output conduit portals A (1517), B (1518), C (1519), and port S1 (1520). As described above, for the sweep ports A, B and C in valve 1500, when the rotary is not pointing to that port, transport medium flows through from the input conduit portals A1, B1, and C1 (1504, 1505, 1506) and out the output conduit ports A, B and C (1517, 1518, and 1519).

Figure 15D:
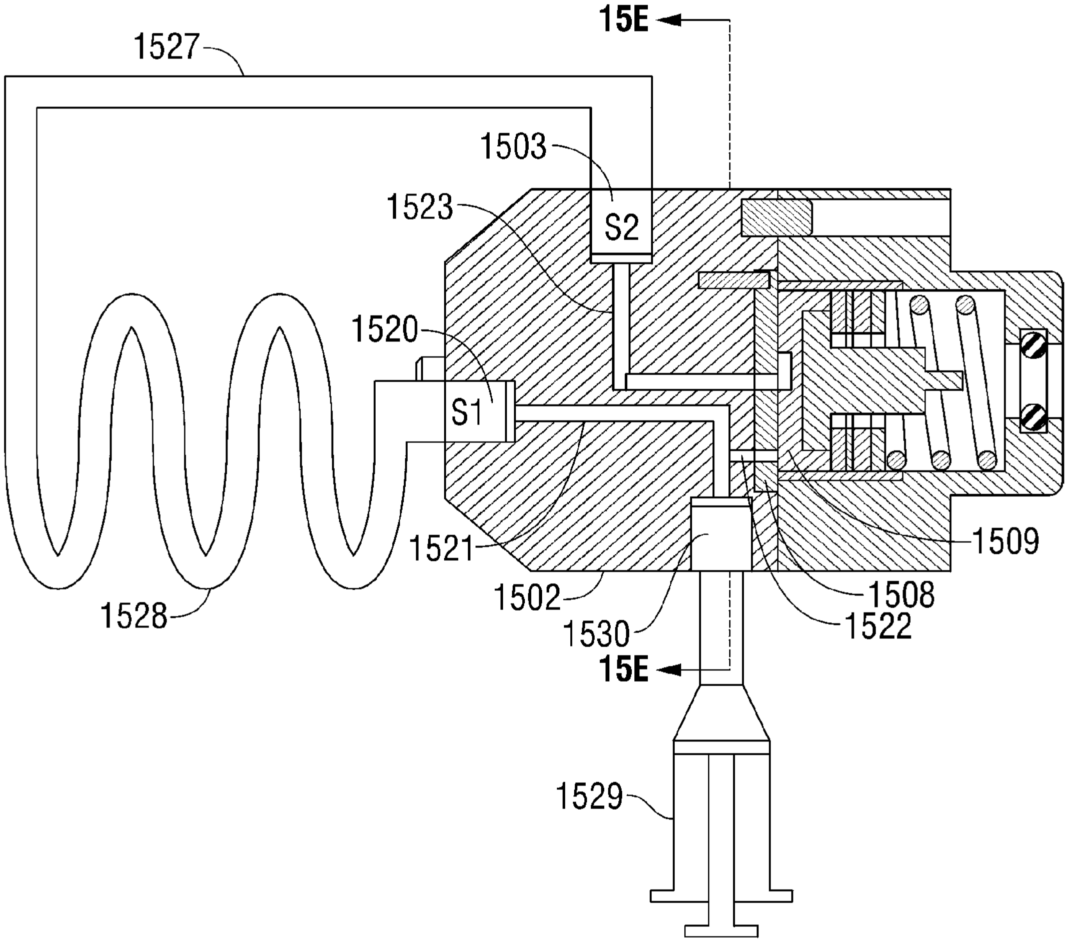
Figure 15E:
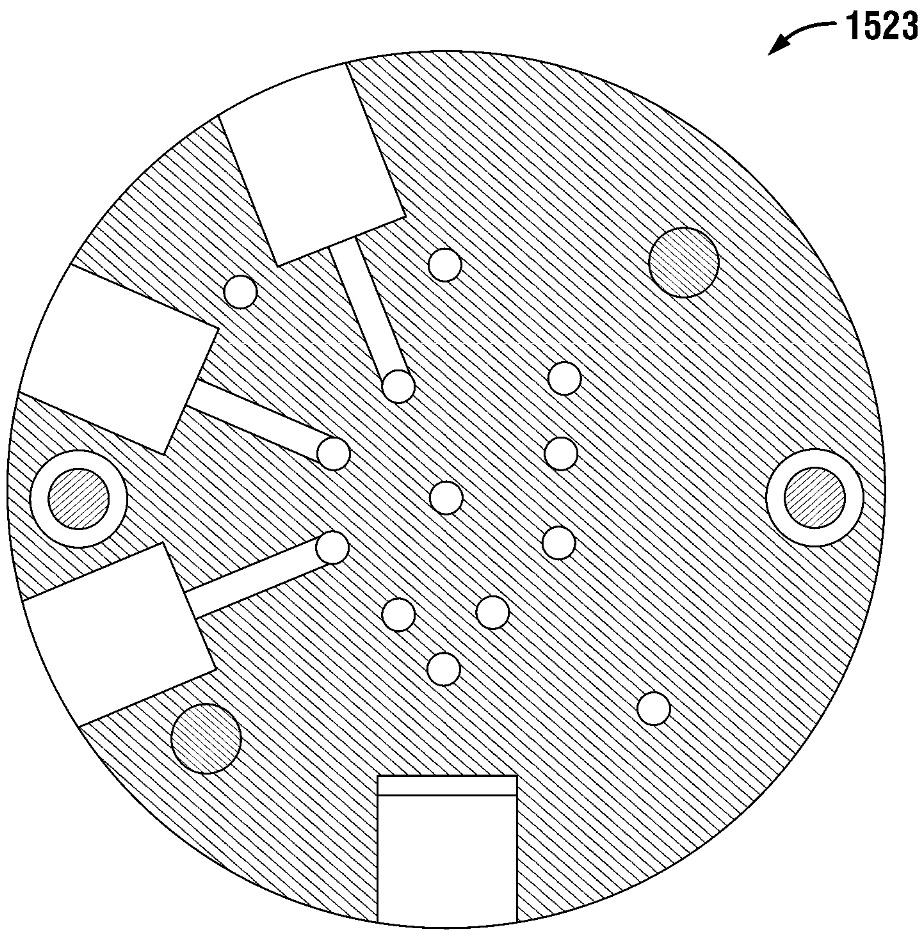

FIG. 15D illustrates the cross-section view along an axis shown in FIG. 15C. FIG. 15D shows an exemplary syringe pump 1529 connected to syringe port 1530, an exemplary isolation loop 1528 connected to port S1 (1520), and a bypass conduit 1527 connecting isolation loop 1528 and port S2 (1503). In an embodiment bypass conduit 1527 is part of isolation loop 1528. Also shown are internal conduits 1521, 1522, and 1523. Internal conduit 1521 provides fluid communication between center port S1 (1520) and syringe port 1530; internal conduit 1522 provides fluid communication between internal conduit 1521 through a penetration in the outer radius of stator 1508 to rotor 1509. Internal conduit 1523 provides fluid communication between port S2 (1503) and the stator 1508 center penetration to rotor 1509. FIG. 15E shows cross-sectional view of valve 1500 along axis B-B in FIG. d and illustrates sweep ports A-C and penetrations corresponding to the penetrations in stator 1508.

FIG. 15D illustrates two modes of operation of valve 1500. When it is desired to aspirate transport medium directly into syringe pump 1529 bypassing isolation loop 1528, the valve is turned to position H. In position H, there is an open conduit within the outer radius between port H, connected to a source of transport medium (not shown), and inner conduit 1522, and the center port in rotor 1509 is blocked. The syringe pump can then aspirate transport medium directly from internal conduit 1522.

When it is desired to inject the contents of injection loop 1528, for example sample, into an analysis stream, for example, the analysis stream connected to ports C (1519) and C1 (1506), the internal conduit 1521 is first filled with transport medium. The system is primed through a series of syringe actions. These actions are initiated with the valve at port G, the sample/waste position, the prime pump engaged, the syringe is moved to full dispense position. This eliminates any unknown content from the isolation loop. The prime pump is turned off and the valve is moved to the H port and the syringe 1529 moved to the fully aspirated position. This action aspirates transport media from reservoir 1112 to port H of valve 1500 through the rotor 1509 and a penetration in the outer circle of stator 1508 through internal conduits 1522 and 1521 in to the syringe The syringe 1529 contents are then emptied by placing the valve 1500 at port G, the sample/waste position, engaging the prime pump, and moving the syringe to full dispense position. This eliminates any unknown content from the isolation loop and rinses the syringe. The prime pump is turned off, the valve 1500 is moved to the H port, and the syringe 1529 moved to the partially aspirated position and is ready to operate. After the system is primed, the rotary is turned to position C. In position C internal conduit 1522 is blocked but internal conduit 1523 is connected to flow sweep port C through the center port in stator 1508 and via rotor 1509. Applying syringe pump 1529 therefore expels transport medium from internal conduit 1521 into isolation loop 1528, which expels sample from isolation loop 1528 through conduit 1527, through port S2 (1503), through internal conduit 1523, and through stator 1508 into rotor 1509 and through to port C where it joins with transport medium flowing into input conduit portal C1 (1506) ($C_{in}$) and the stream containing transport medium and sample flows out through output conduit portal C (1519) ($C_{out}$).

In an embodiment the system utilizes a single port to both acquire a sample for analysis and to discharge waste. The valve 1500 utilizes port G as the sample/waste position, Sample is primed by engaging the prime pump, inserting the input tube into a sample vessel and either through a time interval or a sample sensing technique stopping the pump when the sample is primed. In this process any excess sample is discharged to waste. The syringe 1246 via the isolation loop 1245 and valve 1500 can now aspirate sample and inject the needed volumes into any or all of the system analytical streams. When all needed injections of a particular sample have been completed the input tube can be lifted from the sample vessel, either manually or through the actions of an autosampler, the valve 1500 is moved port G, the sample/waste position, the prime pump engaged, and the syringe is moved to full dispense position This eliminates any unwanted content from the isolation loop and valve as well as provides an internal rinse with the transport media. Additional rinsing can be accomplished during this process by placing the input tube in a rinse agent. The prime pump is turned off when the waste/rinse cycle has been completed. After rinsing is completed the sample cycle can be repeated.

The Abstract of the disclosure is written solely for providing the United States Patent and Trademark Office and the public at large with a means by which to determine quickly from a cursory inspection the nature and gist of the technical disclosure, and it represents one preferred implementation and is not indicative of the nature of the invention as a whole.

While some implementations of the invention have been illustrated in detail, the invention is not limited to the implementations shown; modifications and adaptations of the above embodiment may occur to those skilled in the art. Such modifications and adaptations are in the spirit and scope of the invention as set forth herein.

What is claimed is:

1. A system for regulating flow in a fluidic device, comprising:

a fluidic conduit adapted and configured to transport an analytical stream comprising a transport medium, the analytical stream comprising the transport medium having a transport medium flow rate;

a sample injector adapted and configured to inject sample into the analytical stream;

a first reagent injector adapted and configured to inject a first reagent into the analytical stream;

a first reaction device adapted and configured to comprise an analyte produced by a reaction in the analytical stream between the sample and the first reagent, the first reaction device coupled to the fluidic conduit downstream of the sample injector and the first reagent injector;

an analyte detector downstream of the first reaction device; and a pumping system and flow control module adapted and configured to maintain a constant flow rate of the analytical stream comprising the analyte at the analyte detector, comprising:

a transport medium pump;

a transport medium sensor; and a transport medium flow rate controller.

2. The system for regulating flow in a fluidic device of claim 1, wherein the pumping system and flow control module is upstream of the sample injector and the first reagent injector.

3. The system for regulating flow in a fluidic device of claim 1, wherein the transport medium sensor comprises a pressure sensor.

4. The system for regulating flow in a fluidic device of claim 1, wherein the transport medium flow rate controller comprises a variable sized orifice.

5. The system for regulating flow in a fluidic device of claim 1, wherein the transport medium pump comprises a non-peristaltic pump.

6. The system for regulating flow in a fluidic device of claim 1, further comprising:

a second reagent injector adapted and configured to inject a second reagent into the analytical stream;

a second reaction device adapted and configured to comprise a second analyte produced by a reaction in the analytical stream between the sample, the first reagent, and the second reagent.

7. The system of claim 5 wherein the non-peristaltic pump comprises a rotary pump.

* * * * *